United States Patent [19]

Meyer, Jr. et al.

[11] Patent Number: 5,652,359
[45] Date of Patent: Jul. 29, 1997

[54] OLIGONUCLEOTIDES CONTAINING N-METHYL THIOLATED BASES HAVING ANTIVIRAL ACTIVITY

[75] Inventors: Rich B. Meyer, Jr., Woodinville; Alexander A. Gall, Bothell, both of Wash.; Arthur D. Broom, Salt Lake City, Utah

[73] Assignee: Epoch Pharmaceuticals, Inc., Washington, D.C.

[21] Appl. No.: 162,590

[22] Filed: Dec. 2, 1993

[51] Int. Cl.$^6$ .......................... C07H 21/02; A61K 31/70
[52] U.S. Cl. ........................................................ 536/25.5
[58] Field of Search ............................. 536/25.5; 514/44

[56] References Cited

U.S. PATENT DOCUMENTS 5,416,203  5/1995  Lestinger ........................ 536/25.34

OTHER PUBLICATIONS

Chan et al. J. Gen. Virol. 52:241–249, 1981, month not available.

Amarnath et al. Biochimica et Biophysica Acta 474:16–23 (1977), month not available.

Amarnath et al. Biochemistry 15(20):4386–4389, 1976, month not available.

Iribarren et al. Proc. Natl. Acad. Sci. 87:7747–7751, 1990.

Broom A. D. et al., "Synthesis and PMR Studies of some Methylated 6–Thiopurine Nucleosides (1)", J. Heterocyclic Chem. 12, 171–174 (1975), month not available.

Saamu Shibahara et al., "Inhibition of human immunodeficiency virus (HIV–1) replication by synthetic oligo–RNA", Nucleic Acid Research, vol. 17, No. 1, pp. 239–252 (1989), month not available.

*Primary Examiner*—Gary L. Kunz
*Attorney, Agent, or Firm*—Klein & Szekeres, LLP

[57] ABSTRACT

Oligonucleotides containing 1-N-alkyl-6-thiopurine, 3-N-alkyl-4-thiopyrimidine and 5-N-alkyl-4-thiopyrazolopyrimidine bases and the corresponding 2'-O-alkylated or allylated nucleotides demonstrate potent antiviral activity in several assays, including the human immunodeficiency virus reverse transcriptase enzyme assay. The oligonucleotides of the invention contain approximately 5 to 99 nucleotide units, and may include, in addition to the above-noted N-alkylated and thiolated heterocyclic bases, the naturally occurring pyrimidine and purine bases.

9 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1..28

( D ) OTHER INFORMATION: /mod_base= OTHER
/ note= "Each of nucleotides 1 through 28 is
derived from a 9-(2'-O-methyl-1-beta-D-
ribofuranosyl)-1-methyl-6-thiopurine with a
3'- phosphate.

( i x ) FEATURE:
( A ) NAME/KEY: modified_base
( B ) LOCATION: 29
( D ) OTHER INFORMATION: /mod_base=OTHER
/ note= "Nucleotide 29 is derived from
9-(2'-O- methyl-1-beta-D-ribofuranosyl)-1-methyl-6
- thiopurine with a 3'-phosphate to which is
attached a (CH2)6-OH tail.

( x i ) SEQUENCE DESCRIPTION: SEQ ID NO:1:

NNNNNNNNN NNNNNNNNN NNNNNNNNN 29

( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i x ) FEATURE:
( A ) NAME/KEY: modified_base
( B ) LOCATION: 1..28
( D ) OTHER INFORMATION: /mod_base=OTHER
/ note= "Each of nucleotides 1 through 28 is
derived from 9-(2'-O-methyl-1-beta-D-
ribofuranosyl)-1-methyl-6-thiopurine with a
3'- phosphate.

( i x ) FEATURE:
( A ) NAME/KEY: modified_base
( B ) LOCATION: 29
( D ) OTHER INFORMATION: /mod_base=OTHER
/ note= "Nucleotide 29 is derived from
9-(2'-O- methyl-1-beta-D-ribofuranosyl)-1-methyl-6
- thiopurine with a 3'-phosphate to which is
attached a (CH2)16-OH tail.

( x i ) SEQUENCE DESCRIPTION: SEQ ID NO:2:

NNNNNNNNN NNNNNNNNN NNNNNNNNN 29

( 2 ) INFORMATION FOR SEQ ID NO:3:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i x ) FEATURE:
( A ) NAME/KEY: modified_base
( B ) LOCATION: 1..28
( D ) OTHER INFORMATION: /mod_base=OTHER
/ note= "Each of nucleotides 1 through 28 is
derived from 9-(2'-O-methyl-1-beta-D-
ribofuranosyl)-1-methyl-6-thiopurine with a
3'- phosphorothioate.

( i x ) FEATURE:
( A ) NAME/KEY: modified_base
( B ) LOCATION: 29
( D ) OTHER INFORMATION: /mod_base=OTHER
/ note= "Nucleotide 29 is derived from
9-(2'-O- methyl-1-beta-D-ribofuranosyl)-1-methyl-6
- thiopurine with a 3'-phosphorothioate to which is
attached a (CH2)6-OH tail.

( x i ) SEQUENCE DESCRIPTION: SEQ ID NO:3:

NNNNNNNNN NNNNNNNNN NNNNNNNNN 29

( 2 ) INFORMATION FOR SEQ ID NO:4:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 1..16
    ( D ) OTHER INFORMATION: /mod_base=OTHER
      / note= "Each of nucleotides 1 through 16 is
      derived from 9-(2'-O-methyl-1-beta-D-
      ribofuranosyl)-1-methyl-6-thiopurine with a
      3'- phosphate.

( i x ) FEATURE:
    ( A ) NAME/KEY: modified_base
    ( B ) LOCATION: 17
    ( D ) OTHER INFORMATION: /mod_base=OTHER
      / note= "Nucleotide 17 is derived from
      9-(2'-O- methyl-1-beta-D-ribofuranosyl)-1-methyl-6
      - thiopurine with a 3'-phosphate to which is
      attached a (CH2)6-OH tail.

( x i ) SEQUENCE DESCRIPTION: SEQ ID NO:4:

NNNNNNNNN NNNNNNN                                                                17

( 2 ) INFORMATION FOR SEQ ID NO:5:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 1..36
    ( D ) OTHER INFORMATION: /mod_base=OTHER
      / note= "Each of nucleotides 1 through 36 is
      derived from 9-(2'-O-methyl-1-beta-D-
      ribofuranosyl)-1-methyl-6-thiopurine with a
      3'- phosphate.

( i x ) FEATURE:
    ( A ) NAME/KEY: modified_base
    ( B ) LOCATION: 37
    ( D ) OTHER INFORMATION: /mod_base=OTHER
      / note= "Nucleotide 37 is derived from
      9-(2'-O- methyl-1-beta-D-ribofuranosyl)-1-methyl-6
      - thiopurine with a 3'-phosphate to which is
      attached a (CH2)6-OH tail.

( x i ) SEQUENCE DESCRIPTION: SEQ ID NO:5:

NNNNNNNNN NNNNNNNNN NNNNNNNNN NNNNNNN                                            37

( 2 ) INFORMATION FOR SEQ ID NO:6:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 1..36
    ( D ) OTHER INFORMATION: /mod_base=OTHER
      / note= "Each of nucleotides 1 through 36 is
      derived from 9-(2'-O-methyl-1-beta-D-
      ribofuranosyl)-1-methyl-6-thiopurine with a
      3'- phosphorothioate.

( i x ) FEATURE:
      ( A ) NAME/KEY: modified_base
      ( B ) LOCATION: 37
      ( D ) OTHER INFORMATION: /mod_base=OTHER
        / note= "Nucleotide 37 is derived from
        9-(2'-O- methyl-1-beta-D-ribofuranosyl)-1-methyl-6
        - thiopurine with a 3'-phosphorothioate to which is
        attached a (CH2)6-OH tail.

( x i ) SEQUENCE DESCRIPTION: SEQ ID NO:6:

NNNNNNNNN NNNNNNNNN NNNNNNNNN NNNNNNN                         3 7

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1..36
        ( D ) OTHER INFORMATION: /mod_base=OTHER
          / note= "Each of nucleotides 1 through 36 is
          derived from 9-(2'-O-methyl-1-beta-D-
          ribofuranosyl)-1-methyl-6-thiopurine with a
          3'- phosphate.

( i x ) FEATURE:
        ( A ) NAME/KEY: modified_base
        ( B ) LOCATION: 37
        ( D ) OTHER INFORMATION: /mod_base=OTHER
          / note= "Nucleotide 37 is derived from
          9-(2'-O- methyl-1-beta-D-ribofuranosyl)-1-methyl-6
          - thiopurine with a 3'-phosphate to which is
          attached a tail derived from cholesterol connected
          to the 3'- phosphate through a "linking group"derived
          from 4- hydroxy-2-hydroxymethylpyrrolidine and a carbonyl
          connecting group.

( x i ) SEQUENCE DESCRIPTION: SEQ ID NO:7:

NNNNNNNNN NNNNNNNNN NNNNNNNNN NNNNNNN                         3 7

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1..2
        ( D ) OTHER INFORMATION: /mod_base=OTHER
          / note= "Each of nucleotides 1 and 2 is derived
          from 9-(2'- O-methyl-1-beta-D-ribofuranosyl)-1-
          methyl-6- thiopurine with a 3'-phosphorothioate.

( i x ) FEATURE:
        ( A ) NAME/KEY: modified_base
        ( B ) LOCATION: 3..34
        ( D ) OTHER INFORMATION: /mod_base=OTHER
          / note= "Each of nucleotides 3 through 34 is
          derived from 9-(2'-O-methyl-1-beta-D-
          ribofuranosyl)-1-methyl-6-thiopurine with a
          3'- phosphate.

( i x ) FEATURE:
        ( A ) NAME/KEY: modified_base
        ( B ) LOCATION: 35..36
        ( D ) OTHER INFORMATION: /mod_base=OTHER
          / note= "Each of nucleotides 35 and 36 is derived
          from 9-(2'- O-methyl-1-beta-D-ribofuranosyl)-1- methyl-6- thiopurine with a 3'-phosphorothioate.

(ix) FEATURE:
    (A) NAME/KEY: modified_base
    (B) LOCATION: 37
    (D) OTHER INFORMATION: /mod_base=OTHER
        / note= "Nucleotide 37 is derived from
        9-(2'-O- methyl-1-beta-D-ribofuranosyl)-1-methyl-6
        - thiopurine with a 3'-phosphate to which is
        attached a (CH2)6-OH tail.

(xi) SEQUENCE DESCRIPTION: SEQ ID NO:8:

NNNNNNNNN NNNNNNNNN NNNNNNNNN NNNNNN        37

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1..32
        (D) OTHER INFORMATION: /mod_base=OTHER
            / note= "Each of nucleotides 1 through 32 is
            derived from 9-(2'-O-methyl-1-beta-D-
            ribofuranosyl)-1-methyl-6-thiopurine with a
            3'- phosphate.

(ix) FEATURE:
        (A) NAME/KEY: modified_base
        (B) LOCATION: 33
        (D) OTHER INFORMATION: /mod_base=OTHER
            / note= "Nucleotide 33 is derived from
            9-(2'-O- methyl-1-beta-D-ribofuranosyl)-1-methyl-6
            - thiopurine with a 3'-phosphate to which is
            attached a (CH2)6-OH tail.

(xi) SEQUENCE DESCRIPTION: SEQ ID NO:9:

NNNNNNNNN NNNNNNNNN NNNNNNNNN NNN        33

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1..32
        (D) OTHER INFORMATION: /mod_base=OTHER
            / note= "Each of nucleotides 1 through 32 is
            derived from 9-(2'-O-methyl-1-beta-D-
            ribofuranosyl)-1-methyl-6-thiopurine with a
            3'- phosphorothioate.

(ix) FEATURE:
        (A) NAME/KEY: modified_base
        (B) LOCATION: 33
        (D) OTHER INFORMATION: /mod_base=OTHER
            / note= "Nucleotide 33 is derived from
            9-(2'-O- methyl-1-beta-D-ribofuranosyl)-1-methyl-6
            - thiopurine with a 3'-phosphorothioate to which is
            attached a (CH2)6-OH tail.

(xi) SEQUENCE DESCRIPTION: SEQ ID NO:10:

NNNNNNNNN NNNNNNNNN NNNNNNNNN NNN        33

OLIGONUCLEOTIDES CONTAINING N-METHYL THIOLATED BASES HAVING ANTIVIRAL ACTIVITY

BACKGROUND OF THE INVENTION

1. Technical Field

The present invention is in the field of oligonucleotide compounds of biological activity. More particularly, the present invention is in the field of oligonucleotide compounds which include N-methyl thiolated heterocyclic bases and have antiviral activity.

2. Brief Description of the Prior Art

Nucleosides which contain other than the major naturally occurring heterocyclic bases and related derivatives have been used in the prior art as antiviral agents, for example for treatment of herpes simplex infections. In the present state-of-the-art virtually all drugs utilized for treatment of infection of humans by the human immunodeficiency virus (HIV) are also nucleosides or nucleosides analogs, with 3'-azido-3'-deoxythymidine (AZT) and 2',3'-dideoxycytidine (DDC) serving as examples.

The HIV virus is a retrovirus which carries the virus genom in RNA rather than DNA form. Replication of the HIV virus requires the utilization of a reverse transcriptase enzyme which, in essence, makes a DNA copy of the virus genome which is then incorporated into the DNA of the infected human cells. Several of the therapeutic agents or their metabolic products such as the AZT triphosphate have been shown to be inhibitors of the HIV reverse transcriptase enzyme. The drugs currently used for treatment of HIV infections in humans, are however quite toxic. As is well known, while the state-of-the-art drugs provide some benefit, they are incapable of curing or definitely halting the progress of an advanced stage HIV infection in humans. It is well known, that more effective chemotherapeutic agents are needed for the treatment of HIV infections in humans.

Human cytomegalovirus is a DNA virus which primarily causes respiratory problems and blindness. Ganciclovir (DHPG) is a drug which is used in the state-of-the-art for treatment of humans infected with this virus. It is still considered desirable in the art to develop further chemotherapeutic agents for treatment of by human cytomegalovirus infections.

Certain thiolated purines, pyrimidines and related heterocyclic, bases and the corresponding nucleosides (such as ribosides and deoxyribosides) have been known in the art for a long time. Generally speaking, in these compounds an oxo function (O) of a naturally occuring heterocycle is replaced by a thio (S) group. 6-Thiopurine (also known as 6-mercaptopurine), 6-thio-2-aminopurine ("thioguanine"), 4-thio-2-oxopyrimidine ("thiouracil") and 4-thio-2-oxo-5-methylpyrimidine ("thiothymidine) serve as examples. 6-Thiopurine is a potent inhibitor of an enzyme involved in the biosynthesis of the purine bases which are incorporated into nucleic acids, and although it has been used as drug in the chemotherapy of cancer, it is considered quite toxic. N-methyl derivatives of the above-noted thiolated purines and pyrimidines and their nucleosides have also been known in the prior art, with 1-N-methyl-6-thiopurine serving as an example. (See Broom A. D. et al. J. Heterocyclic Chem. 12, 171–174 (1975)).

Relatively recently, polyribonucleotides of 1-N-methyl-6-thioinosinic acid, of 1-N-methyl-6-thioguanylic acid and of 6-thioguanylic acid (the latter complexed with polycytidylic acid) having molecular weight of $10^5$ to $10^6$ daltons were discovered in the prior art to be agents capable of inhibiting growth of HIV in certain human cell lines. The polyribonucleotides of 1-N-methyl-6-thioinosinic acid is described by E. W. Chan et al. in J. Gen. Virol. 1981, 52, 291–299. The polyribonucleotide of 1-N-methyl-6-thioguanylic acid is disclosed by V. Amarnath et al. in Biochim. Biophys. Acta 1977, 479, 16–23. The complex of poly-6-thioguanylic acid with polycytidylic acid as an antitumor agent is described by V. Amarnath et al. in Biochemistry 1976 15, 4386–4389.

Certain oligo[(2'-O-methyl)ribonucleoside phosphorothioates] were reported as weak inhibitors of the replication of the HIV virus. (Saamu Shibahara et al. Nucleic Acid Research, Volume 17, Number 1, pp239–252 (1989)).

SUMMARY OF THE INVENTION

The principal object of the present invention is to provide oligonucleotide compounds of potent antiviral activity, and particularly to provide oligonucleotide compounds which have activity against the human immunodeficiency (HIV) virus.

In accordance with the present invention oligonucleotide compounds are provided where the oligonucleotide has the formula

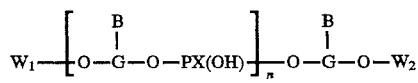

where X is O or S;

n is an integer between 5 and 99;

G represents a sugar moiety consisting of a pentofuranose, hexofuranose or of a pentopyranose, or an isosteric analog thereof, said sugar moiety being linked to the aglycon B with a glycosidic bond, B is an aglycon selected from a group consisting of a heterocyclic base naturally found in nucleic acids and a modified heterocyclic base which is selected from the group having the formula (1), formula (2), formula (3) and formula (4),

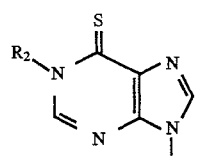

formula (1)

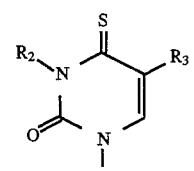

formula (2)

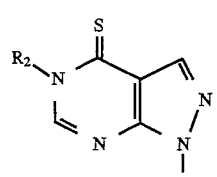

formula (3)

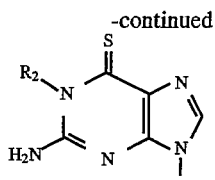

formula (4)

where $R_2$ is $C_1$–$C_6$ alkyl, $C_2$–$C_6$ alkenyl or $C_2$–$C_6$ alkynyl;

$R_3$ is H, $C_1$–$C_4$ alkyl, $C_1$–$C_4$ alkenyl, or $C_1$–$C_4$ alkynyl;

$W_1$ is H or $Y_1$OXP(OH)—;

$W_2$ is H, or $Y_2$OXP(OH)—;

$Y_1$ and $Y_2$ independently are H, —$(CH_2)_m$OH, $(CH_2)_m$NH$_2$, a lipophilic group, or cholesterol having an appendant connecting group attached thereto, where m is an integer between 2–25, and where at least approximately 30% of the nucleotide units of said oligonucleotide include the modified heterocyclic base as the aglycon.

The present invention also relates to the processes of preparing the novel oligonucleotide compounds, to pharmaceutical compositions which include the novel oligonucleotides as their active ingredient and to the processes of treating mammals, including humans, afflicted with a viral infection, particularly with HIV, herpes simplex or human cytomegalovirus infection, with the pharmaceutical compositions containing the novel oligonucleotides.

DESCRIPTION OF THE PREFERRED EMBODIMENTS

General Embodiments

Broadly speaking the oligonucleotides of the present invention have the structure

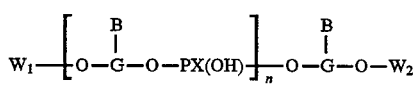

where the various symbols are defined as in the Summary of the Invention. An important distinguishing feature of the oligonucleotides of the invention is that at least approximately 30 percent (30%) of the heterocyclic bases B are not the naturally occurring major bases of nucleic acids (uracil, thymine, cytosine, adenine or guanine) but rather they are modified in that they contain a thio function and an $\underline{N}$—$C_1$–$C_6$ alkyl, $\underline{N}$—$C_1$–$C_6$ alkenyl or $\underline{N}$—$C_1$–$C_6$ alkynyl group. More specifically, the modified heterocyclic bases in the oligonucleotide of the invention correspond to the structures set forth in formula (1), formula (2), formula (3), and formula (4) found in the Summary of the Invention.

Formula (1) depicts 1-$\underline{N}$-alkyl, alkenyl or alkynyl 6-thiopurine bases; formula (2) depicts 3-$\underline{N}$-alkyl, alkenyl or alkynyl 4-thiouracil, 4-thiothymine or other 5-alkyl, 5-alkenyl or 5-alkynyl 4-thiouracil bases; formula (3) depicts 5-$\underline{N}$-alkyl, alkenyl or alkynyl 4-mercaptopyrazolopyrimidine bases, and formula (4) depicts 1-$\underline{N}$-alkyl, alkenyl or alkynyl 6-thioguanine bases. Among the foregoing groups, the 1-$\underline{N}$-alkyl, alkenyl or alkynyl 6-thiopurine derivatives are presently preferred in accordance with the invention. With regard to the $\underline{N}$-alkyl, alkenyl or alkynyl groups ($R_2$) in accordance with the present invention, methyl, ethyl and allyl groups are preferred. With regard to the $R_3$ group of formula (2), compounds are preferred where $R_3$ is H or methyl.

Oligonucleotide compounds having only one kind of modified heterocyclic base selected from the formulas (1) through (4) are within the scope of the invention. Alternatively, oligonucleotide compounds having modified heterocyclic bases of more than one kind (selected from the formulas (1) through (4)) are also within the scope of the invention. However, oligonucleotides wherein all modified heterocyclic bases are of the same formula and oligonucleotides where at least approximately 50% of the bases are modified, are presently preferred.

The heterocyclic bases of the oligonucleotides of the present invention which are not modified as set forth in formulas (1) through (4), are selected primarily from the naturally occurring major base components of nucleic acids (uracil, thymine, cytosine, adenine and guanine). Minor naturally occurring nucleic acid component bases can also be incorporated in the oligonucleotides of the present invention. Within one oligonucleotide molecule of the invention the naturally occurring bases may all be the same, or may vary within the scope described above. In accordance with the invention all heterocyclic bases (B) of the oligonucleotide molecule may be modified bases (that is of formula (1) through (4)), and all bases may have the same structure. In fact, such "homooligomers" comprising one modified base in each oligomer are preferred, and constitute the herein described specific examples.

The heterocyclic base B (aglycon) is attached to the sugar moiety represented by G in the formula, as set forth in the Summary of the Invention. The sugar moiety (G) in the oligonucleotides of the invention has the feature that, in addition to being linked to the base B by a glycosidic (carbon-to-nitrogen) bond, it is linked at least to two derivatized hydroxyl groups which link each nucleotide unit to the adjacent nucleotides with phospodiester or phosphorothioate diester linkages. Sugar moieties which may be incorporated into the oligonucleotides of the invention include pentofuranoses, hexofuranoses and pentopyranoses, such as the corresponding furanoses and pyranoses derived from D-ribose, 2-deoxy-D-ribose, D-arabinose, and D-glucose. Even a carbocyclic analog of a sugar, which is otherwise isosteric with a pentofuranose, hexofuranose or pentopyranose may form the "sugar moiety" G in accordance with the present invention. In the presently preferred embodiments of the invention furanoses of D-pentose sugars, and particularly the pentofuranose forms of 2-deoxy-D-ribose, D-arabinose and 2-$\underline{O}$ alkylated D-ribose are preferred.

With regard to the glycosidic bond between the heterocyclic base B and the sugar moiety G, this bond may be either of α or of β configuration in accordance with the present invention. The designation of α and β for the configuration of the glycosidic bond is well established and understood by those skilled in the art. With regard to D-arabinose sugars however, when such are incorporated into the oligonucleotides of the present invention, the glycosidic bond of α configuration is presently preferred, whereas for 2-O alkylated, alkenylated or alkynylated D-ribose sugars the β configuration is presently preferred.

With reference to the general formula of the oligonucleotides as set forth in the Summary of the Invention, the symbol X represents oxygen or sulphur. In other words, both phosphate and phosphorothioates are within the scope of the invention. In accordance with the invention the oligonucleotides may contain either only one of the two of the phosphate and phosphorothioate linkages, or both types may be present in the same oligonucleotide molecule. In this regard it is noted that phosphorothioate linkages are known in the art to lend increased stability to oligonucleotides against nuclease enzymes. In accordance with one preferred embodiment of the present invention at least one of the phospodiester groups of each of the two 3-nucleotide terminal sequences of the oligonucleotide contains a phosphorothioate group. In a specific example described below the last two nucleotide units on each terminus of that example are linked with phosphorothioate linkages.

In the general structure depicting the oligonucleotide of the present invention, shown in the Summary of the Invention, the left side of the structure symbolizes the 5'-end of the oligonucleotide chain, and the right side symbolizes the 3'-end. Either the 5' end nucleotide or the 3' end nucleotide, or both, may bear a phosphate or phosphorothioate group, or may end with the corresponding 5' or 3' hydroxyl group. Preferably, however, the 5'-end lacks a phosphate or phosphorothioate group ($W_1$ in the general formula is preferably H), and the 3'-end preferably bears a phosphate or phosphorothioate to which a lipophilic group, preferably a relatively short chain (2–6 carbons) hydroxyalkyl group, is attached ($W_2$ is $Y_2OXP(OH)$—).

The term "lipophilic group" in this regard is well understood by those skilled in the art of medicinal chemistry, and means a group whose chemical make-up provides it with high affinity to lipid phase matter. The term "lipophilic group", in the context of being attached to an oligonucteotide, refers to a group having high hydrocarbon content thereby giving the group high affinity to lipid phases. A lipophilic group can be a relatively long chain alkyl or cycloalkyl (preferably n-alkyl) group having approximately 2 to 30 carbons. The alkyl group may terminate with a hydroxy or primary amine "tail". Preferred examples for such lipophilic n-alkyl groups attached to the 3'-terminus (and optionally to the 5' terminus) of the oligonucleotide are $(CH_2)_n$—OH or $(CH_2)_n$—$NH_2$, where n preferably ranges between 2 to 16. Cholesterol is another example of a lipophilic group. Other examplary lipophilic groups of "steroid" type structure are cholic acid, progesterone and estradiol.

The lipophilic group may be connected to the terminus of the oligonucleotide through various linkages such as a phosphorothioester or phosphoramidate linkages, which are shown here for the specific example where the lipophilic group is cholesterol. The oxygen atom of the hydroxyl function of cholesterol which is attached to the A ring of the steroid skeleton is marked with an asterisk.)

Oligo-3'—OP(OH)O—S—$(CH_2)_n$—NHCO—O*chol (phosphorothioester)

Oligo-3'—OP(OH)O—NH—$(CH_2)_n$—NHCO—O*chol (phosphoroamidate)

In the foregoing two examples n ranges between 1 to approximately 8 in value and the respective groups —S—$(CH_2)_n$—NHCO and —NH—$(CH_2)_n$—NHCO— can be termed "appandant connecting groups". These are groups which are derived from a bifunctional molecule and which allow covalent linking of the lipophilic group (such as cholesterol) to the phosphate or phosphorothioate terminus of the oligonucleotide. The bifunctional molecule may, for example, have an amine and a thiol, an amine, and a hydroxyl, or a thiol and a hydroxy functionality, which are then reacted with the lipophilic group and with an activated form of the 3'-phosphate terminus. The appendant connecting group can also be defined (and will be understood as such by those skilled in the art) as a group which covalently connects the lipophilic group to the phosphate or phosphorothioate terminus without destroying the ability of the connected lipophilic group to perform its intended function.

Alternatively, cholesterol (or other lipophilic group) may be connected to the 3' or 5' terminus of the oligonucleotide through a linking molecule that has a primary hydroxyl, secondary hydroxyl and an amine functionality, each such function having different reactivity. An example for such a trifunctional linking molecule is 4-hydroxy-2-hydroxymethylpyrrolidine, another example is 3-amino-1,2-propanediol. When such a trifunctional linking molecule is used, the cholesterol or other lipophilic group may be attached to the primary amine through a "an appendant connecting group", and the primary hydroxyl group of the linking molecule may be attached to the 3'-phosphate terminus of the oligonucleotide. The secondary hydroxyl group of the just described linking molecule (such as 4-hydroxy-2-hydroxymethylpyrrolidine or 3-amino-1,2-propanediol) may be utilized to attach the molecule to a solid phase support allowing step-by-step oligonucleotide synthesis on an automatic synthesizer, in accordance with the state-of-the art. An example of cholesterol linked to the 3'-terminus of the oligonucleotide via a carbamate linkage and 4-hydroxy-2-hydroxymethylpyrrolidine is shown below. The carbamate linkage, linking cholesterol with the amine function of 4-hydroxy-2-hydroxymethylpyrrolidine is derived from chloroformate. In a broad sense the entire trifunctional linking molecule plus the "CO" group of this example serve as an "appendant connecting group" linking the exemplary cholesterol, or other lipophilic group to the 3'-phosphate or phosphorothioate terminus of the oligonucleotide.

Alternatively, a lipophilic group can be connected by a "carbamate" linkage, or by some other group, to the amine function of 3-amino-1,2-propanediol which in turn is linked to the 3'-phosphate terminus with its primary hydroxyl group.

Referring now to Formula 5 and TABLE 1 below, specific examples of preferred oligonucleotide compounds of the present invention are disclosed. As a general description of these specific preferred compounds it should be noted that these preferred compounds are homooligomers where the heterocyclic base is 1-methyl-6-thiopurine and where the sugar is 2'-O-methyl-D-ribose in the β furanose configuration. The 5'-terminus of each of the preferred oligonucleotides of Formula 5 is unsubstituted, that is it ends with the 5'—OH group. The 3'-terminus, on the other hand, has a phosphate or phosphorothioate group which is connected to hexanol, hexadecanol or a cholesterol "tail" as indicated below.

TABLE 1

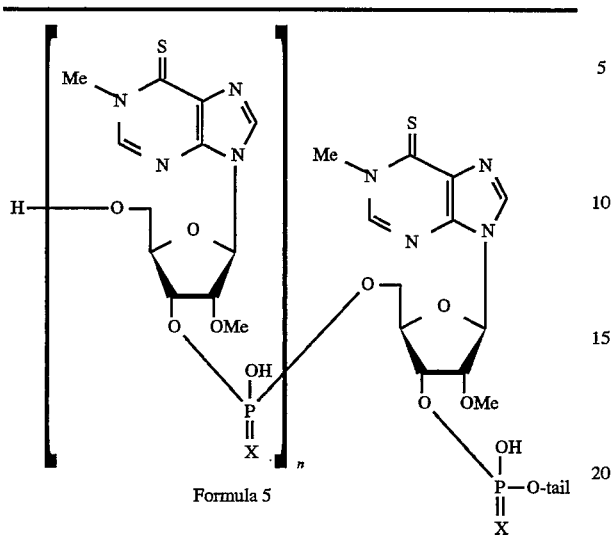

Formula 5

| Compound No. | n | X | 3'-tail | $IC_{50}(\mu M)$ |
|---|---|---|---|---|
| 1 | 28 | O | $(CH_2)_6-OH$ | 0.4 |
| 2 | 28 | O | $(CH_2)_{16}-OH$ | 0.2 |
| 3 | 28 | S | $(CH_2)_6-OH$ | 0.06 |
| 4 | 16 | O | $(CH_2)_6-OH$ | 3.0 |
| 5 | 36 | O | $(CH_2)_6-OH$ | 0.04 |
| 6 | 36 | S | $(CH_2)_6-OH$ | 0.11 |
| 7 | 36 | O | R' | 0.016 |
| 8 | 36 | 1,2 S; 3-34 O; 35,36 S | $(CH_2)_6-OH$ | 0.009 |
| 9 | 32 | O | $(CH_2)_6-OH$ | 0.022 |
| 10 | 32 | S | $(CH_2)_6-OH$ | 0.037 |
| Nucleoside* | | | | ~100 |

*The nucleoside is the "monomer" 9-(2'-O-methyl-1-β-D-ribofuranosyl)-1-methyl-6-thiopurine.

The group R' in Table 1 represents the cholesterol "tail" of Compound 7 which is connected to the 3'-terminal phosphate through a "linking group" derived from 4-hydroxy-2-hydroxymethylpyrrolidine and carbonyl connecting group. With respect to Compound 8, Table 1 indicates that counting from the 5'-terminus, the first two and the last two nucleotides contain phosphorothioate linkages and that the remaining nucleotides contain "natural" phosphodiester linkages. The $IC_{50}$ numbers in Table 1 refer to the concentration of the compound which gives 50% inhibition of replication of HIV in a cell culture of human peripheral blood mononuclear (PBM) cells. The test in which these data were obtained is described below.

Reaction Scheme 1

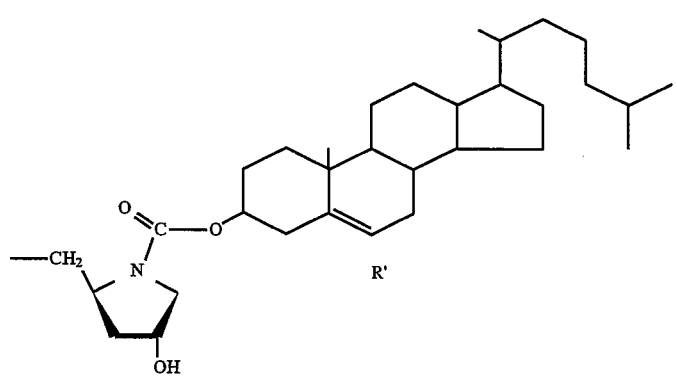

R'

-continued
Reaction Scheme 1

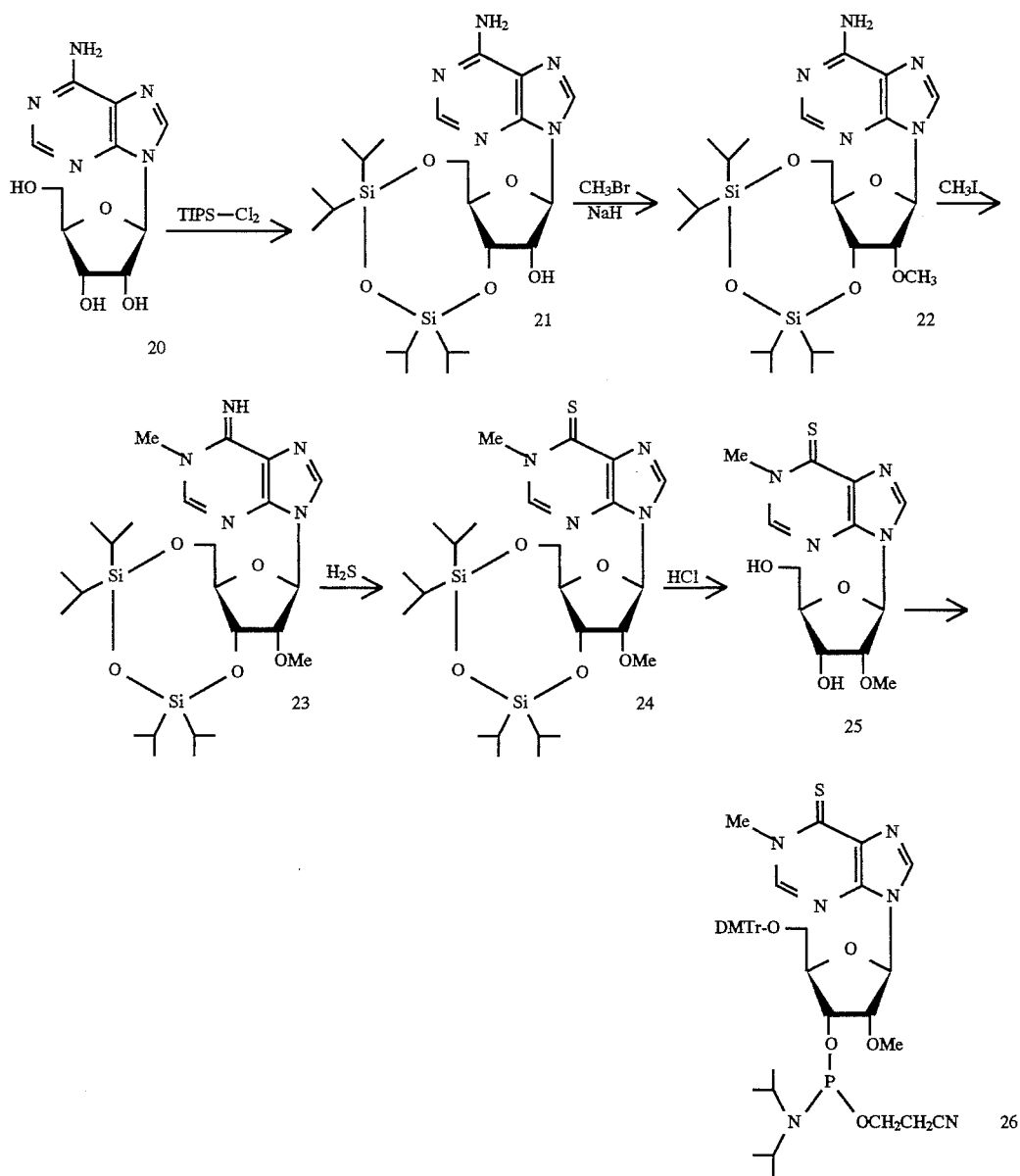

Referring now to Reaction Scheme 1, an exemplary synthetic route for obtaining the 6-thiopurine monomer building blocks of the oligonucleotides of the present invention, and particularly the synthesis of 2'-O-methyl-β-D-ribofuranosyl-1-N-methyl-6-thiopurine is disclosed. In accordance with this scheme, the nucleoside adenosine (Compound 20) is reacted with tetraisopropyldisiloxane dichloride (TIPS) to protect the 3' and 5' hydroxyl groups. This reaction provides Compound 21. Methylation with methyl bromide first yields the 2'-O-methyl derivative (Compound 22) which is methylated further with methyl iodide to yield the 2'-O-1-N-dimethyl derivative (Compound 23. The methyl (or in analogous compounds other alkyl) group in the N-1 position renders the 6-imino group susceptible to replacement with sulphur when Compound 23 is reacted with hydrogen sulfide. Treatment with fluoride ion or with concentrated hydrochloric acid of the blocked 6-thiopurine derivative 24 removes the disiloxane blocking group to yield the nucleoside 2'—O-methyl-1-β-D-ribofuranosyl-1-N-methyl-6-thiopurine (Compound 25). The nucleoside 25 is thereafter reacted with dimethoxytriphenylmethyl chloride (DMT-Cl) to block the 5' position. Thereafter, the β-cyanoethyl-diisopropyl-phosphoroimidate moiety is introduced by standard reactions to provide the nucleoside derivative 26 which is suitable for "standard" oligonucleotide synthesis in an automated synthesizer utilizing a solid support.

The synthetic steps described in Reaction Scheme 1 can be utilized, with such modifications which will be readily apparent to those skilled in the art, for the synthesis of other 1-N-methyl-6-thiopurine nucleosides/nucleotides, which are building blocks of the novel oligonucleotides of the present invention. For example, the 2'-deoxyriboside of 1-N-methyl-6-thiopurine is readily prepared from 2'-deoxyadenosine in substantial accordance with Reaction Scheme 1.

Reaction Scheme 2

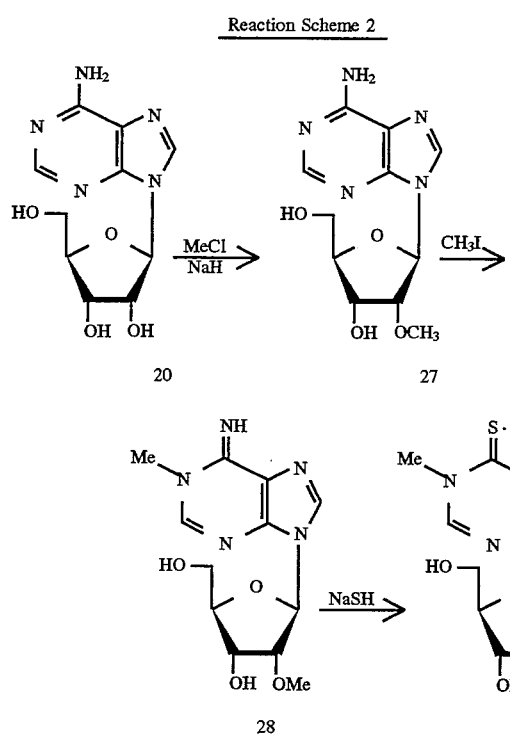

Reaction Scheme 2 discloses the presently preferred method for preparing 1-N-,2'-O-dimethyl-6-thioinosine (Compound 25). In accordance with this method, adenosine (Compound 20) is reacted with methylchloride in a polar aprotic solvent, such as dimethylformamide (DMF) or dimethylacetamide (DMA) in the presence of strong base, such as sodium hydride. The resulting 2'-O-methyl adenosine is reacted, without isolation, with iodomethane to introduce the methyl group to the 1-N-position. After the treatment with iodomethane a crude product is obtained which contains approximately 60% of the desired 1-N-,2'-O-dimethyladenosine intermediate, and also contains some 1-N-,3'-O-dimethyladenosine as well as monomethylated derivatives. The crude product is reacted at a moderately elevated temperature (approximately 45° C.) with anhydrous sodium sulfide in anhydrous dimethylformamide, and the resulting crude product is purified by chromatography to yield the desired 1-N-,2'-O-dimethyl-6-thioinosine (Compound 25).

Reaction Scheme 3

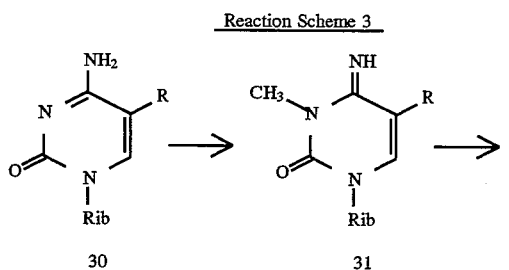

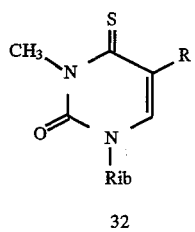

Referring now to Reaction Scheme 3, the synthesis of 4-thiopyrimidine monomer building blocks of the novel oligonucleotides is disclosed. In accordance with this scheme, the nucleoside cytidine (Compound 30), or 5-alkyl cytidine is first methylated in the N-3 position, and thereafter reacted with hydrogen sulfide to provide the corresponding 3-N-methyl-4-thiouridine or its 5-alkyl derivative (Compound 32). These nucleosides can then be used in state-of-the-art reactions to provide derivatives suitable for the synthesis of oligonucleotides in an automatic synthesizer. The 3-N-alkyl-4-thiopyrimidine nucleosides, nucleotides and oligonucleotides are, however, more sensitive to base than the analogous purine derivatives. Therefore, the oligonucleotides containing these 3-N-alkyl 4-thiopyrimidine bases have to be removed from the solid support used for oligonucleotide synthesis by a DBU-catalyzed elimination reaction in acetonitrile, rather than by treatment with aqueous or methanolic ammonia.

Reaction Scheme 4

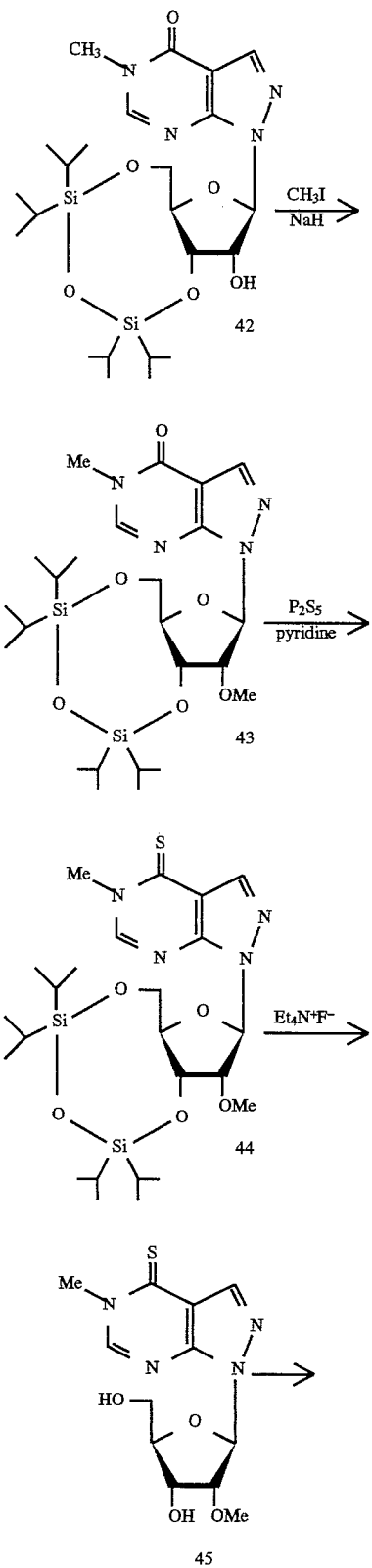

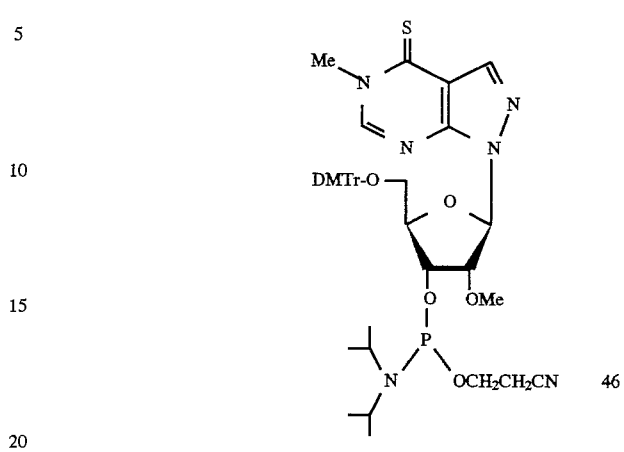

Reaction Scheme 4 discloses a general synthetic route to the N-alkyl-4-thiopyrazolo [3,4-d]pyrimidine nucleoside monomers of the oligonucleotides of the present invention. The scheme is illustrated with the riboside of the heterocyclic base known as allopurinol, but it should be understood that with such appropriate modifications which would be apparent to those skilled in the art, the reactions of this scheme can also be performed on other glycosides of allopurinol. Moreover, the scheme shows methylation in the 5-position of the pyrazolopyrimidine base. However instead of methylation other alkylation, or even more generally speaking introduction of the $R_2$ group as this group is defined in connection with Formula 3, can also be performed in analogous steps.

The riboside of allopurinol (Compound 40) is available by known literature procedures. Compound 40 is reacted with methyl iodide in the presence of base to provide the allopurinol riboside methylated in the 5-position (Compound 41). Compound 41 is reacted with tetraisopropyldisiloxane dichloride (TIPS) to protect the 5'- and 3'-hydroxyl groups, yielding Compound 42. Compound 42 is methylated on the 2'-hydroxyl function, in the presence of strong base, such as sodium hydride, to yield (Compound 43). Compound 43 is reacted with phosphorous pentasulfide in pyridine to convert the 4-oxo group into the desired 4-thio group. The resulting 2'-,5-dimethyl, 3',5'-tetraisopropyldisiloxy-4-thiopyrazolopyrimidine riboside (Compound 44) is subjected to treatment with fluoride ion (tetraethylammonium fluoride) to remove the tetraisopropyldisiloxy blocking group, and to yield 2'-,5-dimethyl-4-thiopyrazolopyrimidine riboside (Compound 45). This nucleoside (Compound 45) can be converted to the corresponding 5'-O-dimethoxytriphenylmethyl-3'-O-β-cyanoethyl-diisopropyl-phosphoroamidite (Compound 46) by reaction steps which are well known in the art.

Reaction Scheme 5

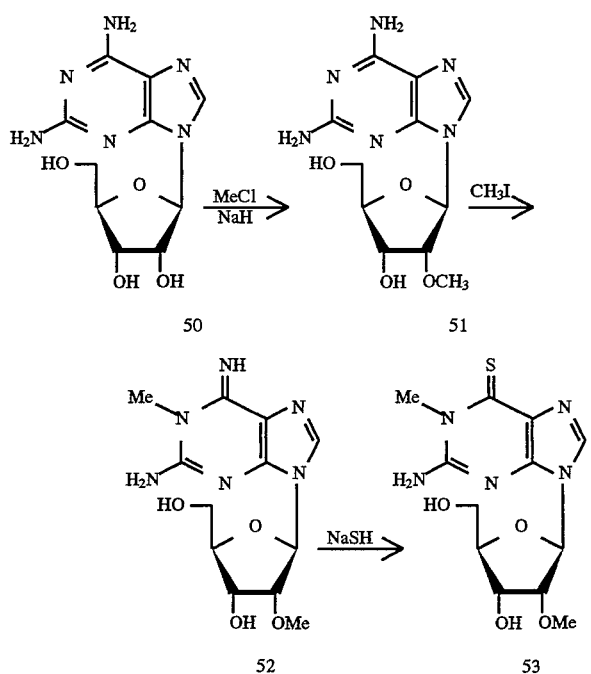

Reaction Scheme 5 discloses a general synthetic route to the 1-N-methyl-6-thioguanine nucloside monomers of the oligonucleotides of the present invention. This exemplary synthetic route, like the synthetic route of Reaction Scheme 4, is also illustrated with the example of a "riboside" and with "methyl" as the group $R_2$ of Formula 4. Thus, the nucleoside guanosine (Compound 50) is methylated with methylchloride in a polar aprotic solvent, such as dimethylformamide (DMF) or dimethylacetamide (DMA) in the presence of strong base, such as sodium hydride. The resulting 2'-O-methyl guanosine (Compound 51) is reacted with iodomethane to introduce the methyl group to the 1-N-position. The resulting 2'-O-N_1-dimethyl guanosine (Compound 52) is reacted with anhydrous sodium sulfide in an anhydrous polar aprotic solvent such as dimethylformamide, and the resulting crude product is purified by chromatography to yield the desired 1-N-,2'-O-dimethyl-2-amino-6-thiopurine riboside (Compound 53).

Oligonucleotide synthesis

As noted above the nucleosides are 5'-dimethoxytritylated, following known procedures, to give around 85% yield, and the 3'-phosphoramidite is made using diisopropylaminocyanoethylchlorophosphite (as described in "Oligonucleotide Synthesis: A Practical Approach", M. J. Gait, Ed., IRL Press, p. 23–34 (1984), with diisopropylethylamine in methylene chloride. The phosphoramidite is made into a 0.2N solution in acetonitrile and placed on the automated DNA synthesizer.

Oligonucleotides are removed from the DNA synthesizer in dimethoxytritylated form by using 30% ammonia at 55° C. for 6 hours in case of thiopurines and thiopyrazolopyrimidines. Because of their greater sensitivity to base, the oligonucleotides containing thiopyrimidines are removed in a DBU-catalyzed elimination reaction. The oligonucleotides are typically evaporated to dryness under vacuum with a small amount of sodium bicarbonate added to prevent acidification, and redissolved in water and purified by HPLC typically using 15–55% acetonitrile in 0.1N triethylammonium acetate over 20 minutes. The desired oligonucleotide is collected and evaporated to dryness, then it is redissolved in 80% aqueous acetic acid for 90 minutes to remove the dimethoxytrityl group. Desalting can be accomplished with a G25 Sephadex® column, by collecting appropriate fractions. The fractions are typically concentrated, brought to a specific volume, a dilution reading taken to ascertain overall yield and an analytical HPLC done to assure purity. Oligonucleotides are typically frozen at 20° C. until use.

Formulations, Modes of Administration

The oligonucleotides of the present invention are active in inhibiting or substantially reducing the propagation of the human immudeficiency virus, herpes simplex virus and the human cytomegalovirus, and are therefore useful for the treatment of diseases and conditions caused by these and other vital agents. Generally speaking, the active oligonucleotides will be administered to humans and other mammals suffering from a viral disease, in the form of a suitable pharmaceutical composition which is formulated for a specific mode of administration, and which contains an effective amount of the active oligonucleotide or a pharmaceutically acceptable salt thereof. The effective amount of the active ingredient oligonucleotide of this invention in the formulation or dosage form depends on the nature and severity of the viral disease or condition to be treated, and may vary from patient to patient. Generally speaking, a dose in the range of approximately 1 to 50 mg of active compound per kg body weight of the recipient, per day is contemplated. The active ingredient and therefore the pharmaceutical composition may be administered systemically in the form of pills, tablets or other dosage forms suitable for oral administration, by injections for intravenous or subcutaneous administration, or in pharmaceutical compositions adapted for absorption through the mucous membranes. Topical administration in the form of creams, ointments and lotions is also contemplated. The active ingredient, namely the oligonucleotide of the present invention, in these compositions is novel. However, the remaining components of the pharmaceutical compositions with which the novel active ingredients are admixed to form a dosage unit for a specific form of administration are well known and established in the art, and need not be described here. The novel oligonucleotide antiviral agents of the present invention can also be administered in combination with other, known antiviral agents.

ANTI-VIRAL ACTIVITY

The oligonucleotides of the present invention have potent anti-viral activity. The anti-viral activity of these compounds against human immunodeficiency virus (HIV), herpes simplex (HSV) and the human cytomegalovirus (HCMV) can be demonstrated in the following assays and procedures.

HSV PLAQUE REDUCTION ASSAY. (herpes simplex)

z Vero cells were plated in 24-well tissue culture plates at density of approximately $4 \times 10^5$ cells per well (2 cm$^2$). HSV-1 (KOS strain) or HSV-2 (333 strain) were added at 80 PFU per well in a total volume of 100 uL per well. Ater 1 hour adsorption period at 37° C., an overlay containing 1% methylcellulose, 2% dialyzed fetal bovine serum, and the drug concentrations in RPMI medium was added. After incubation for 48 hours at 37° C., the methylcellulose overlay was removed and the cells were stained with 0.8% crystal violet in 50% ethanol.

Table 2 indicates the results, obtained in this assay with certain examplary oligonucleotides of the invention. The oligonucleotides are identified by their respective "compound number" (as in Table 1). IC$_{50}$ indicates that concentration (expressed in micromols) of the oligonucleotide which caused 50% inhibition of the propagation of the herpes simplex 1 and herpes simplex 2, virus, respectively.

TABLE 2

| Compound # | IC$_{50}$ (µM) | |
|---|---|---|
| | HSV-1 | HSV-2 |
| 2 | >0.5 | >0.5 |
| 3 | 1–5* | 0.1–1* |
| 4 | >2 | >2 |
| 5 | 0.86 | 0.42 |
| 6 | >1 | 0.57 |
| 9 | >1 | 0.48 |

*At this drug concentration full inhibition was obtained

HSV DNA POLYMERASE ASSAY.

HSV DNA polymerases were assayed as described by Ostrander M., and Cheng Y. C., (1980) BIOCHEM. BIOPHYS. ACTA 609:232–245. The standard assay mixture (total volume 50 uL) contained 25 mM Tris-HCl pH 8, 10 mM MgCl$_2$, 0.5 mM dithiothreitol, 0.5 mg/mL BSA, 200 mM KCl, 100 ug/mL activated calf thymus DNA, 0.1 mM each dATP, dCTP, dGTP, 5 uM [$^3$H]dTTP (2 Ci/mmol), 4–5×10$^{-4}$ units of enzyme, and different drug concentrations. After incubation at 37° C. for 30 minutes, the reaction mixture was spotted on 2.4 cm Whatman GF/A glass fiber filter discs and trichloroacetic acid-insoluble radioactivity was measured.

One unit of DNA polymerase activity is defined as the amount of enzyme which catalyzes the incorporation of 1 nanomol of dTMP into activated DNA/30 min. Table 3 shows the results obtained in this assay. IC$_{50}$ is that concentration (expressed in micromoles) of the novel oligonucleotide which results in 50% inhibition of the enzyme.

TABLE 3

| Compound # | IC$_{50}$ (µM) | |
|---|---|---|
| | HSV-1 | HSV-2 |
| 1 | 0.1 | 0.1 |
| 2 | 1.6 | 0.7 |
| 3 | 0.2 | 0.07 |
| 4 | >1 | >1 |
| 5 | 0.08 | 0.05 |
| 6 | >1 | 0.47 |
| 9 | >1 | 0.46 |
| SdC28* | 0.03 | 0.09 |

*SdC28 is a homo-oligonucliotide with 28 deoxycytidine residues connected by phosphorothioate linkages (5'-[dCyd-3'-P(S)(O)]$_{27}$-dCyd).

HIV REVERSE TRANSCRIPTASE ASSAY.

HIV-1 reverse transcriptase (RT) was expressed from a recombinant plasmid in bacteria as a 66 and 51 kDa protein dimer as described by D'Aquila R. T. and Summers W. C., (1989) J. ACQUIRED IMMUNE DEFIC SYNDR 2:579–587.

The standard reaction mixture for the RNA-dependent enzyme assays contained in a 50 uL volume: 50 mM Tris-HCl, pH 7.8, 50 mM KCl, 6 mM MgCl$_2$, 0.1 mg/mL heat-inactivated bovine serum albumin, 1 mM dithiothreitol, 0.5 0D$_{260}$ units/mL template-primer Poly(rC) oligo(dG)$_{12-18}$, 10 uM [$^3$H]dGTP and 3.3×10$^{-3}$ units of HIV-1 RT. A unit was defined as the amount of enzyme necessary to incorporate 1 nanomol of [$^3$H]dTMP into the Poly(rA)-oligo (dT)$_{10}$ template in 1.0 min at 37° C. The samples were incubated for 30 minutes at 37° C., and all reactions were carried out in the linear range. Aliquot of 40 uL were spotted on glass fiber filters (Whatman GF/A) and processed for determination of trichloroacetic acid-insoluble radioactivity as described by Cheng Y. C., Dutschman G. E., Bastow K. F., Sarngadharan M. G., and Ting R. Y. C. (1987) J. BIOL CHEM 262:2187–2189. Poly(rA)-oligo(dT)$_{10}$ was used as template-primer.

Table 4 indicates the results obtained in this assay with examplary oligonucleotides of the invention. The oligonucleotides are identified by their respective "compound number". IC$_{50}$ indicates that concentration of the oligonucleotide (expressed in nanomoles) which caused 50% inhibition of the enzyme.

TABLE 4

| Compound # | IC$_{50}$ (nM) | |
|---|---|---|
| | HIV-1 | HIV-2 |
| 1 | 33 ± 5 | 84 ± 3 |
| 2 | 65 ± 12 | 94 ± 6 |
| 3 | 20 ± 6 | 43 ± 6 |
| 4 | 189 ± 25 | 98 ± 3 |
| 5 | 32 ± 3 | 33 ± 3 |
| 6 | 67 ± 0.2 | |
| 9 | 77 ± 2.5 | 0.46 |
| SdC28* | 15 ± 4 | 71 ± 11 |

*SdC28 is a homo-oligonucliotide with 28 deoxycytidine residues connected by phosphorothioate linkages (5'-[dCyd-3'-P(S)(O)]$_{27}$-dCyd).

IN VITRO HUMAN CYTOMEGALOVIRUS INHIBITION ASSAY

Cells MRC-5, an immortalized line of diploid, human (male) embryonic lung cells were used. These can be obtained from the American Type Culture Collection, Rockville, Md.

Virus Human cytomegalovirus (HCMV), strain AD-169 were used. These can be obtained from the American Type Culture Collection, Rockville, Md.

Medium Growth medium for the MRC-5 cells consisted of Basal Medium Eagle (BME) (GIBCO BRL, Research Products Division, Life Technologies, Inc., Grand Island, N.Y. was the source of all media) with 10% fetal bovine serum (FBS) (Hyclone Laboratories, Logan Utah), 0.035% NaHCO$_3$. Antibiotics were not used in the growth media. Test medium for dilution of HCMV and for preparation and dilution of compounds for the experiments was DMEM, 2% FBS, 0.1% NaHCO$_3$, 50 µg gentamicin/ml.

All compounds were prepared and diluted to the concentrations indicated in test medium. Growth medium was decanted from established monolayers of MRC-5 cells in 24-well tissue culture plates (Corning Glass Works, Corning, N.Y.). One ml of virus, diluted in test medium, was placed in each well except those to be used for cell controls. One ml of sterile test medium was placed in each of these cell control wells. Virus was allowed to adsorb to the cells while plates were centrifuged at 2200 rpm for 30 minutes at room temperature. Medium was aspirated from each well of the plates and 0.8 ml of the proper compound dilution was placed in each of the test wells (2 wells/dilution). Test medium without compound was added (0.8 ml/well) to each cell control and virus control well. Plates were placed in an incubator at 37° C. in a moist atmosphere of 5% CO$_2$, 95% air until plaques could be distinguished in the virus control wells. Cells were observed microscopically for morphological changes due to compound cytotoxicity before the medium was aspirated from all wells and the cells stained by adding 0.3 ml of 0.2% crystal violet in 10% buffered formalin to each well. After 15 minutes, the stain was aspirated, the plates were rinsed in running tap water until the water was clear, and the plates were inverted and dried at room temperature. Plaques were counted by use of a dissecting microscope.

$ED_{50}$ and $CD_{50}$ values were calculated by regression analysis of the viral plaque data and the visual cell toxicity data, respectively. $ED_{50}$ is the concentration of the test compound at which the average number of plaques is reduced to 50% of that seen in the virus controls (effective dose, 50% endpoint). $CD_{50}$ is the concentration halfway between those at which 100% and 0% cytotoxicity are seen. The Therapeutic Index (TI) is obtained from these data: TI=$CD_{50}$/$ED_{50}$. Table 5 indicates the percentage of plaque reduction obtained in this assay with varying concentration of test compound, Compound 1 of the invention and with the established drug ganciclovir (DHPG). The $ED_{50}$, $CD_{50}$ and TI data of Compound 1 and of ganciclovir are also indicated.

TABLE 5

| Concentration of 1 (µg/ml) | # of plaques | % reduction |
| --- | --- | --- |
| 50 | 16.0 | 65 |
| 15 | 23.5 | 49 |
| 5 | 16.0 | 65 |
| 1.6 | 19.5 | 58 |
| 0.5 | 39.0 | 15 |
| 0.16 | 44.0 | 0 |
| 0.05 | 44.0 | 0 |

$ED_{50}$ (µg/ml) 1.3; , $CD_{50}$ (µg/ml) > 50; TI > 38.

| Concentration of DHPG (µg/ml) | # of plaques | % reduction |
| --- | --- | --- |
| 10 | 0.0 | 100 |
| 3.2 | 10.5 | 77 |
| 1.0 | 33.5 | 27 |
| 0.32 | 39.5 | 14 |

$ED_{50}$ (µ/ml) 1.7; , $CD_{50}$ (µg/ml) > 1000(previous data); TI > 588.

INHIBITION OF HIV VIRUS REPLICATION IN HUMAN PERIPHERAL BLOOD MONONUCLEAR (PBM) CELLS

Cell Culture. Human PBM cells from healthy HIV-1 seronegative and hepatitis B virus seronegative donors were isolated by Ficoll-Hypaque discontinuous gradient centrifugation at 1,000× g for 30 minutes, washed twice in phosphate-buffered saline (pH 7.2; PBS), and pelleted at 300× g for 10 min. Before infection, the cells were stimulated by phytohemagglutinin (PHA) at a concentration of 6 µg/ml for 2–3 days in RPMI 1640 medium supplemented with 15% heat-inactivated fetal calf serum, 1.5 mM L-glutamine, penicillin (100 U/ml), streptomycin (100 µg/ml), and 4 mM sodium bicarbonate buffer.

Viruses. HIV-1 (strain LAV-1) was obtained from Dr. P. Feorino (Emory University, Atlanta, Ga.). The virus was propagated in human PBM cells using RPMI 1640 medium, as described previously (McDougal, J. S., Cort, S. P., Kennedy, M. S. Cabridilla, C. D., Feorino, P. M., Francis, D. P., Hicks, D., Kalyanaramen, V. S. and Martin, L. S. (1985): Immunoassay for the detection and quantitation of infectious human retrovirus, lymphadenopathy-associated virus (LAV). J. Immun. Meth. 76:171–183) without PHA or fungizone and supplemented with 26 units/ml of recombinant interleukin-2 (Cetus Corporation, Emeryville, Calif.), 7 µg/ml DEAE-dextran (Pharmacia, Uppsala, Sweden), and 370 U/ml anti-human leukocyte (alpha) interferon (ICN, Lisle, Ill.). Virus obtained from cell-free culture supernatant was titrated and stored in aliquots at −70° C. until use.

Inhibition of Virus Replication in Human PBM cells. Uninfected PHA-stimulated human PBM cells were infected in bulk with a suitable dilutions of virus. The mean reverse transcriptase (RT) activity of the inocula was about 60,000 dpm RT activity/$10^6$ cells/10 ml. This represents, by a limiting dilution method in PBM cells, a multiplicity of infection of about 0.01. After 1 hour, the cells were uniformly distributed among 25 $cm^2$ flasks to give a 5 ml suspension containing about 2×$10^6$ cells/ml. The drugs at twice their final concentrations in 5 ml of RPMI 1640 medium, supplemented as described above, were added to the cultures. The cultures were maintained in a humidified 5% $CO_2$-95% air incubator at 37° C. for six days after infection at which point all cultures were sampled for supernatant RT activity. Previous studies had indicated that maximum RT levels were obtained at that time.

Reverse Trancriptase (RT) Activity Assay. One ml supernatant from each culture was clarified from cells at 300× g for 10 minutes. Virus particles were pelleted at 12,000 rpm for 2 hours using a Jouan refrigerated microcentrifuge (Model MR 14.11) and suspended in 100 82 1 of virus disrupting buffer (50 mM Tris-HCl, pH 7.8,800 mM NaCl, 20% glycerol, 0.5 mM phenylmethyl sulfonyl fluoride, and 0.5% Triton X-100). The RT assay was performed in 96-well microtiter plates, as described by Spira, T. J., Bozeman, L. H., Holman, R. C., Warfield, D. T., Phillips, S. K., and Feorino, P. M. (1987): Micromethod for assaying the reverse transcriptase of LAV-HTLV-III/lymphadenopathy-associated virus. J. Clin. Microbiol. 25: 97–99. The reaction mixture, which contained 50 mM Tris-HCl pH 7.8,9 mM $MgCl_2$, 5 mM dithiothreitol, 4.7 µg/ml $(rA)_n·(dT)_{12-18}$, 140 µM dATP, and 0.22 µM [$^3$H]TTP (specific activity 78.0 Ci/mmol, equivalent to 17,300 cpm/pmol; NEN Research Products, Boston, Mass.), was added to each well. The sample (20 µl) was added to the reaction mixture which was then incubated at 37° C. for 2 hours. The reaction was terminated by the addition of 100 µl 10% trichloroacetic acid (TCA) containing 0.45 mM sodium pyrophosphate. The acid-insoluble nucleic acids which precipitated were collected on glass filters using a Skatron semi-automatic harvester (setting 9). The filters were washed with 5% TCA and 70% ethanol, dried, and placed in scintillation vials. Four ml of scintillation fluid (Ecolite, ICN, Irvine, Calif.) were added and the amount of radioactivity in each sample was determined using a Beckman liquid scintillation analyzer (model LS3801). The results were expressed in dpm/ml of original clarified supernatant. The procedures for the anti-HIV-1 assays in PBM cells described above have been published (Schinazi, R. F., Cannon, D. L. Arnold, B. H., and Martino-Saltzman, D. (1988): Combinations of isoprinosine and 3'-azido-3'-deoxythymidine in lymphocytes infected with human immunodeficiency virus type 1. Antimicrob. Agents Chemother. 32:1784–1787; Schinazi, R. F., Sommadossi, J. P., Saalmann, V., Cannon, D., Xie, M. -W., Hart, G., Smith, G., and Hahn, E. (1990): Activity of 3'-azido-3'-deoxythymidine nucleotide dimers in primary lymphocytes infected with human immunodeficiency virus type 1. Antimicrob Agents Chemother. 34:1061–1067.

Cytotoxicity Studies in PBM Cells. The drugs were evaluated for their potential toxic effects on uninfected PHA-stimulated human PBM cells. The cells were cultured with and without drug for 24 hours at which time radiolabeled thymidine (0.5 µCi in 20 µl/well) was added. The assay was performed as described previously (Bardos, T. J., Schinazi, R. F., Ling, K-H. J., and Heider, A. R. (1992): Structure-activity relationships and mode of action of 5-mercapto-substituted oligo-and polynucleotides as anti-templates inhibiting replication of human immunodeficiency virus type 1. Antimicrob. Agents Chemother. 36:108–114). Alternatively, cells are counted on day 6 using a hemacytometer or Coulter counter as described previously (Schinazi et al., Antimicrob Agents Chemother, 1990, supra).

Median-Effect Method. $EC_{50}$ and $IC_{50}$ values were obtained by analysis of the data using the median-effect equation of Chou, T. -C., and Talalay, P. (1984): Quantitative analysis of dose-effect relationships: the combined effects of multiple drugs or enzyme inhibitors. Adv. Enz. Regul. 22:27–55. These values were derived from the computer-generated medium effect plot of the dose-effect data using a commercially available program (Chou, J., and T. -C. Chou. (1985): Dose-effect analysis with microcomputers: Quantitation of $ED_{50}$, $LD_{50}$, synergism, antagonism, low-dose risk, receptor binding and enzyme kinetics. A computer software for Apple II Series and IBM-PC and Instruction Manual. Elsevier-Biosoft, Elsevier Science Publishers, Cambridge, U.K.

The results of this assay are shown in Table 1. $IC_{50}$ indicates the concentration of the oligonucleotide compound which results in 50% inhibition of the replication of the HIV virus.

It can be seen from the foregoing description of the assays and Tables 1–5 that the oligonucleotide compounds of the invention are active against the propagation of the HIV, HSV and HCMV viruses. The assay data further indicate that the reverse transcriptase enzyme of the HIV, as well as the DNA polymerase enzyme of the HSV virus is inhibited by the oligonucleotide compounds of the invention. With reference to Table 1, it is noted that all of the oligonucleotides shown therein can be considered very good inhibitors of the replication of HIV-1 in the cell culture assayed. To the best knowledge of the inventors, Compound 8 is the most potent oligonucleotide reported to this date in its ability to elicit a specific biological response in cell culture.

With regard to the assay data shown in Table 5 it is noteworthy that Compound 1 has an $ED_{50}$ value against the replication of HCMV as good as that of the established drug gancyclovir (DHPG) on a weight/volume basis.

SPECIFIC EMBODIMENTS: PREPARATION OF THE OLIGONUCLEOTIDES AND THEIR PRECURSORS 1,2'-N,O-Dimethyl-6-thioinosine (Compound 25) (method 1) and 1-methyl-6-thioinosine.

A mixture of 53.5 g (0.20 mol) of adenosine (Compound 20) and 12.0 g (0.30 mol) of 60% sodium hydride (suspension in oil) in 500 mL of dry N,N-dimethylaceteamide was stirred for 30 min under argon at room temperature and cautiously treated with 0.5 mL (0.03 mol) of water. The mixture was stirred at room temperature for 1 hr to release hydrogen and to form a slurry. The mixture was cooled at –20°, treated with 100 g (2.0 mol) of liquid chloromethane (Aldrich), stirred for 18 hr at room temperature, and partially evaporated at 40°/1 mmHg to 100–120 mL volume, treated with 50 mL of iodomethane, and stirred at room temperature for 40 hr. The resultant oil was poured into a stirred mixture of acetone-ethylacetate (1:1 1 L) and filtered, washed with ethylacetate to give 83 g of white powder. This mixture of N,O-methylated adenosines contained c.a. 60% of 1,2'-N,O-dimethyladenosine, based on HPLC data). The mixture and 28 g of powdered anhydrous NaSH (purchased from Aldrich as NaSH.XH$_2$O and dried in vacuo at 140° for 2 days) was stirred in a 1 L flask with 175 ml of anhydrous DMF at 45° under argon for 4 hours. HPLC at this point showed only small amount of starting material left. A solution of 90 ml of acetic acid in 75 ml of water was added cautiously, and the hydrogen sulfide gas released was absorbed in sodium hydroxide solution. The mixture was filtered and three times water was added and evaporated to dryness. The residue was dissolved in 100 ml of water and purified in a 10 portions on C-18 cartridges (3 sections 40×100 mm, Waters, PrepPak Cartridges, Bondapak C18, 15–20 um, 125A) using Waters PrepPak RCM Base, and eluted with 20% (v/v) methanol (isocratic chromatography), 100 ml/min for 19 min/run. Fractions with 340 nm absorption were collected. A fraction eluted with 20% methanol in 5–6.5 minutes was evaporated to 20 mL to afford 2.0 g (4% yield, based on starting material) of white precipitate characterized as 1-methyl-6-thioinosine, m.p. 196°–200°. $R_f$ 0.27 (Kieselgel TLC plates, EtOAc-acetone-MeOH-H$_2$O 12:1:1:1). $\lambda_{max}$ (0.1M triethylamine-acetate, pH 7.5): 230, 320 nm.

1-N,2'-O-Dimethyl-6-thioinosine was isolated from fractions 7.5–10 min by evaporation and crystallization from 240 mL of water to give 18 g (34% yield based on starting material) of colorless crystals, m.p. 182°–187° (from methanol). $R_f$ 0.30 (Kieselgel TLC plates, EtOAc-acetone-MeOH-H$_2$O 12:1:1:1). $\lambda_{max}$ (0.1M triethylamine-acetate, pH 7.5): 230, 320 nm. The by-product 1-N,2',3'-di-O-trimethyl-6-thioinosine could be isolated from 14–18 min fraction.

N-1,2'-O-Dimethyl-6-thioinosine (Compound 25). Method 2

To a frozen solution (–30°), of 56.5 g (110 mmol) of 3',5'-O-(1,1,3,3-tetraisopropyl-1,3-disiloxanediyl)adenosine (Compound 21) (prepared according to the procedure of: Nucleic Acid Chemistry, part 3, p. 268) in 300 mL of dry DMF was added 6.7 g (170 mmol) of sodium hydride (60% dispersion in oil) and 40 mL (700 mmol) of cold (0°) bromomethane. The mixture was stirred under argon and allowed gradually to warm to 0°, then stirred at this temperature for 1 hr and neutralized by addition of 6 mL of acetic acid. The mixture was concentrated to dryness at 30°/1 mm Hg. The residue was dissolved in 500 mL of ethyl acetate and washed with 50 mL of saturated NaHCO$_3$, then with 50 mL of saturated NaCl. After drying over Na$_2$SO$_4$ with stirring, the solution was filtered and evaporated. The resultant oil was dissolved in 50 mL of DMF, treated with 25 mL of iodomethane for 40 hr at room temperature, and concentrated to dryness at 30°/1 mmHg. The residue was dissolved in 86 mL of methanol and transferred into a 2 L stainless steel bomb. To the bomb were added 55 mL of pyridine, 3.36 g (30 mmol) of 1,4-diazabicyclo[2.2.2]octane (Aldrich) as a catalyst, and 10.8 g (110 mmol) of potassium acetate. The bomb was sealed, charged with 800 g of hydrogen sulfide and heated at 45° with stirring for 70 hr. (The pressure in the bomb should not exceed 600 psi.) After 70 hours the bomb was cooled to room temperature and the hydrogen sulfide distilled into a trap cooled by dry ice. The residual mixture was transferred into a flask and toluene (100 mL) was added and evaporated three times to remove residual pyridine. The residue was dissolved in 500 mL of methanol, and treated with 25 mL of conc. HCl for 33 hr at room temperature. The solution was evaporated to dryness and the residue washed with 2×100 mL of ether. The residue was chromatographed on a Bakerbond C-18 column (5×33 cm) and eluted with 1 L of 1% acetic acid in 30% (v/v) methanol. Fractions with 320 nm absorbtion were combined and evaporated. The residue was dissolved in 100 mL of hot water and cooled to 4°. The resulting precipitate was filtered, washed with cold water and dried in vacuo to give 7.0 g (20% yield) of colorless solid. The compound was recrystallized from methanol m.p. 185°–188°, $R_f$ 0.30 (Kieselgel TLC plates, ethyl acetate-acetone-methanol-water, 12:1:1:1). $\lambda_{max}$ (0.1M triethylammonium-acetate, pH 7.5): 230, 320 nm. Analysis calculated for $C_{12}H_{16}N_4O_4S \cdot 0.5H_2O$: C, 44.85; H, 5.33; N, 17.44; S, 9.98%. Found: C, 44.97; H, 5.34; N, 17.18; S, 9.65%.

1-N-Methyl-3',5'-O-(1,1,3,3-tetraisopropyl-1,3-disiloxanediyl)-6-thioinosine 1-Methyl-6-thioinosine (obtainable by the procedure of P. C. Ratsep, N. C. Mishra, A. D. Broom. Thiopurine Nucleosides: Variations in Hydrophobicity Among $N^1$ Subsituents. *Nucleosides & Nucleotides*, 10(8), pp 1641–1655 (1991)) (4.0 g, 13.4 mmol) was dried by evaporation with pyridine, dissolved in 30 mL of dry pyridine and treated with 4.5 g (14.3 mmol) of 1,3-dichloro-1,1,3,3-tetraisopropyldisiloxane (Aldrich) at room temperature for 24 hr. Thereafter, the mixture was treated with 5 mL of methanol, evaporated to dryness, dissolved in 300 mL of ethyl acetate, and washed with 50 mL of saturated NaCl solution. The EtOAc solution was dried over $Na_2SO_4$, evaporated to dryness and applied to a silica gel column (4×25 cm), eluted with 700 mL of dichloromethane-ethanol (15:1) to afford 7.0 g (96%) of 3',5'-protected nucleoside as a solid foam, $R_f$ 0.43 (Kieselgel TLC plates, chloroform-ethanol, 20:1). $\lambda_{max}$ (0.1M triethylammonium acetate, pH 7.5): 230, (*) 320 nm. Analysis calculated for $C_{23}H_{40}N_4O_5SSi_2$: C, 51.08; H, 7.46; N, 10.36; S, 5.93, Si, 10.39%. Found: C, 50.97; H, 7.54; N, 10.20; S, 5.89, Si, 10.45%.

5'-O-Dimethoxytrityl-N-1,2'-O-Dimethyl-6-thioinosine.

5.1 g (16 mmol) of dry 1.2'-O-dimethyl-6-thioinosine (Compound 25) was stirred under argon with 6.9 g (20 mmol) of 4,4'-dimethoxytritylchloride in 100 mL of dry pyridine at room temperature for 4 hr. The reaction was monitored by TLC. The mixture was treated with 5 mL of methanol and evaporated to dryness. The residue was dissolved in 50 mL of ethyl acetate-triethylamine (4:1) and loaded onto a silica gel column (5×26 cm, preflushed with 10% triethylamine in ethyl acetate). The column was flushed with 500 mL of ethyl acetate-methanol-triethylamine (100:5:1) and the product was eluted with additional 600 mL of the same eluent. Fractions with 320 nm absorbtion were combined and evaporated. The resultant foam was stirred with 150 mL of hexanes to give the title compounds as a fine powder, yield 9.7 g (97%); m.p. 83°–90° (decomp.), $R_f$ 0.43 (Kieselgel TLC plates, ethyl acetate-methanol-triethylamine, 100:5:1). $\lambda_{max}$ (0.1M triethylammonium-acetate, pH 7.5): 228, 320 nm. Analysis: calculated for $C_{33}H_{34}N_4O_6S$: C, 64.48; H, 5.58; N, 9.11; S, 5.22. Found: C, 64.01; H, 5.79; N, 8.73; S, 5.02.

5'-O-Dimethoxytrityl-1,2'-N,O-dimethyl-6-thioinosine-3'-O-(2-cyanoethyl-N,N-diisopropylphosphoramidite (Compound 26)

A solution of 9.7 g (16 mmol) of 5'-O-dimethoxytrityl-1,2'-N,O-dimethyl-6-thioinosine in 270 mL dry dichloromethane and 11 mL of diisopropylethylamine was treated dropwise with 4.7 mL (21 mmol) of 2-cyanoethyl-N,N-diisopropylchlorophosphoramidite (Aldrich), and the mixture was stirred at room temperature under argon. After 1.5 hour, 5 mL of methanol was added and the mixture poured into 1 L of ethyl acetate containing 30 mL of triethylamine. The resultant solution was washed successively with saturated $NaHCO_3$ (2×250 mL) and saturated NaCl (2×250 mL), then dried over anhydrous $Na_2SO_4$ and evaporated to dryness. The residue was dissolved in 40 mL of $CHCl_3$-$NEt_3$ and purified by flash chromatography over a silica gel column (5×24 cm, preflushed with hexanes-triethylamine, 10:1). The column was washed with 500 mL of hexanes-ethyl acetate-triethylamine (10:20:1) and the phosphoramidite eluted with additional 600 mL of the same solvent mixture. Fractions containing crude product were combined, evaporated to dryness and the residue dissolved in 20 mL of dichloromethane-triethylamine (100:1). This solution was added into vigorously stirred hexanes, to afford 7.6 g (57%) of the title compound, m.p. 99°–115° (decomp.), $R_f$ 0.60 (Kieselgel TLC plates, ethyl acetate-dichloromethane-triethylamine, 5:5:1). $\lambda_{max}$ (0.1M triethylammonium acetate, pH 7.5): 234, 320 nm. Analysis calculated for $C_{42}H_{51}N_6O_7PS$: C, 61.90; H, 6.31; N, 10.31; P, 3.80; S, 3.93. Found: C, 62.03; H, 6.53; N, 9.92; P, 3.71; S, 3.69.

2'-O-Allyl-1-methyl-3',5'-O-(1,1,3,3-tetraisopropyl-1,3-disiloxanediyl)-6-thioinosine.

A procedure for 2'-O-allylation of ribonucleotides is described in: Sproat B. S., Iribarren A. M., Garcia R. G. and Beijer B. New Synthetic Routes to Synthons Suitable for 2'-O-Allyloligoribonucleotide Assembly. *Nucleic Acids Research*, vol. 19(4), pp 733–738 (1991)). A mixture of 2.74 g (5.1 mmol) of 1-methyl-3',5'-O-(1,1,3,3-tetraisopropyl-1,3-disiloxanediyl)-6-thioinosine and 1.5 mL (11.5 mmol) allyl ethyl carbonate (Lakhmiri, R., Lhoste, P. and Sinou, D. Allyl Ethyl Carbonate/Palladium (O), A New System for the One Step Conversion of Alcohols into Allyl Ethers Under Neutral Conditions. *Tetrahedron Letters*, vol. 30(35), pp 4669–4672 (1989)) in 15 mL tetrahydrofuran was refluxed for 6 hours under argon with 55 mg of tris(dibenzylideneacetone)dipalladium(O) (Aldrich) and 96 mg of 1,4-bis(diphenylphosphino)butane (Aldrich). The mixture was evaporated to dryness and applied to a column of silica gel (4×26 cm), eluted with 300 mL of ethyl acetate-hexanes (1:1). The title product was obtained as a foam (1.43 g, 48%); $R_f$ 0.37 (Kieselgel TLC plates, hexanes-ethyl acetate, 1:1). $\lambda_{max}$ (0.1M triethylammonium acetate, pH 7.5): 230, 320 nm.

2'-O-Allyl-1-methyl-6-thioinosine.

A mixture of 1.4 g (2.4 mmol) of 2'-O-allyl-1-methyl-3',5'-O-(1,1,3,3-tetraisopropyl-1,3-disiloxanediyl)-6-thioinosine and 7 mL of 1M tetrabutylammonium fluoride in THF was stirred at room temperature for 10 hr for deprotection. The mixture was evaporated to dryness, the residue treated with 50 mL of 2% acetic acid and extracted with 2×10 mL of hexanes. The aqueous, acetic acid solution of the residue was then applied to Bakerbond C-18 column (5×33 cm) and eluted with 1 L of 1% acetic acid in 40% (v/v) methanol. Fractions with 320 nm absorbtion were combined, evaporated, and dried in vacuo to give 0.7 g (86%) of 2'-O-allyl derivative as a foam; $R_f$ 0.25 (Kieselgel TLC plates, ethyl acetate-methanol-triethylamine, 100:10:1). $\lambda_{max}$ (0.1M triethylammonium acetate, pH 7.5): 230, 320 nm.

2'-O-Allyl-5'-O-dimethoxytrityl-1-methyl-6-thioinosine.

2'-O-Allyl-1-methyl-6-thioinosine (0.7 g, 2.07 mmol) was dried by evaporation with pyridine, dissolved in 25 mL of pyridine, and treated with 0.9 g (2.6 mmol) of 4,4'-dimethoxytritylchloride for 6 hr. The mixture was treated with 3 mL of methanol, evaporated to dryness and the residue applied to a column of silica gel (4×17 cm, preflushed with ethyl acetate-triethylamine, 10:1). The product was eluted with 500 mL of ethyl acetate-methanol-triethylamine (100:2:1). The yield was 1.15 g (87%), solid foam; $R_f$ 0.55 (Kieselgel TLC plates, ethyl acetate-methanol-triethylamine, 100:10:1). $\lambda_{max}$ (0.1M triethylammonium acetate, pH 7.5): 230, 320 nm.

2'-O-Allyl-5'-O-dimethoxytrityl-1-methyl-6-thioinosine-3'-O-(2-cyanoethyl-N,N-diisopropylphosphoramidite).

A solution of 1.05 g (1.64 mmol) of 2'-O-allyl-5'-O-dimethoxytrityl-1-methyl-6-thioinosine in 30 mL of dry dichloromethane and 1.2 mL of diisopropylethylamine was treated dropwise with 0.6 mL (2.7 mmol) of 2-cyanoethyl-N,N-diisopropylchlorophosphoramidite (Aldrich), and the mixture was stirred at room temperature under argon for 2 hr. Methanol (0.5 mL), ethyl acetate (170 mL), and triethylamine (5 mL) were added, and the organic layer was washed successively with saturated $NaHCO_3$ (2×75 mL) and saturated NaCl (2×75 mL), dried over anhydrous $Na_2SO_4$ and evaporated to dryness. The residue was applied to a silica gel column (2×32 cm, preflushed with hexanes-triethylamine, 10:1) and eluted with 300 mL of hexanes-ethyl acetate-triethylamine (10:20:1). The product was obtained as a foam, 1.26 g (91%); $R_f$ 0.40 (Kieselgel TLC plates, hexanes-ethyl acetate-triethylamine 10:20:1). $\lambda_{max}$ (0.1M triethylammonium acetate, pH 7.5): 234, 320 nm.

2'-Deoxy-1-methyl-6-thioinosine.

A mixture of 1.3 g (11.6 mmol) of 1,4-diazabicyclo[2.2.2]octene (Aldrich) and 2.1 g (5 mmol) of 2'-deoxy-1-methyladenosine iodide (J. W. Jones, R. K. Robins, Purine Nucleosides. III. Methylation Studies of Certain Naturally Occurring Purine Nucleosides. *J. Am. Chem. Soc.*, vol. 85, pp 193–201 (1963)) in 20 mL of MeOH was placed into a bomb and frozen in a dry ice bath. A cold solution of 45 mL of hydrogen sulfide in 15 mL of pyridine was added and the bomb was sealed and heated at 40° for 60 hr. The solution in the bomb was evaporated, and the residue was transferred into a flask, evaporated further, and the residue dissolved in 50 mL of 1% acetic acid. This solution was filtered onto the top of a Bakerbond C-18 column (5×33 cm) and eluted with 1 L of 1% acetic acid in 30% (v/v) methanol. Fractions with 320 nm absorbtion were combined and evaporated to dryness. The residue was dissolved in 12 mL of hot methanol and allowed to crystallize at −5°, in a freezer. The precipitate was filtered, washed with 2 mL of cold methanol and dried in vacuo to give 0.73 g (52%) of colorless solid, m.p. 141°–230° (decomp), $R_f$ 0.37 (Kieselgel TLC plates, ethyl acetate-acetone-methanol-water, 12:1:1:1). $\lambda_{max}$ (0.1M triethylammonium acetate, pH 7.5): 230, 320 nm. Analysis calculated for $C_{11}H_{14}N_4O_3S$: C, 46.80; H, 5.00; N, 19.85; S, 11.36%. Found: C, 46.53; H, 4.99; N, 19.68; S, 11.07%.

2'-Deoxy-5'-O-dimethoxytrityl-1-methyl-6-thioinosine.

2'-Deoxy-1-methyl-6-thioinosine (0.8 g, 2.83 mmol) was dried by evaporation with pyridine, dissolved in 30 mL of pyridine, and treated with 1.13 g (3.33 mmol) of 4,4'-dimethoxytritylchloride for 3 hr. Methanol (5 mL) and chloroform (100 mL) were added to the mixture. The organic layer was washed with 150 mL of saturated $NaHCO_3$, dried over $Na_2SO_4$, concentrated, and the residue was applied to a column of silica gel (2×35 cm, preflushed with dichloromethane-triethylamine, 10:1). The product was eluted with 300 mL of ethyl acetate-acetonitrile-triethylamine (100:20:1). The yield was 0.7 g (42%). $R_f$ 0.30 (Kieselgel TLC plates, ethyl acetate-acetonitrile-triethylamine, 100:20:1). $\lambda_{max}$ (0.1M triethylammonium acetate, pH 7.5): 228, 320 nm.

2'-Deoxy-5-O-Dimethoxytrityl-1-methyl-6-thioinosine-3'-O-(2-cyanoethyl-N,N-diisopropylphosphoramidite).

A solution of 0.67 g (1.15 mmol) of 2'-deoxy-5'-O-dimethoxytrityl-1-methyl-6-thioinosine in 30 mL dry dichloromethane and 0.55 mL of diisopropylethylamine was treated dropwise with 0.3 mL (1.34 mmol) of 2-cyanoethyl-N,N-diisopropylchlorophosphoramidite (Aldrich), and the mixture was stirred at room temperature under argon for 1 hr. Methanol (5 mL), ethyl acetate (110 mL), and triethylamine (3 mL) were added, and the organic layer was washed successively with saturated $NaHCO_3$ (2×55 mL) and sat NaCl (2×55 mL), dried over anhydrous $Na_2SO_4$ and evaporated to dryness. The residue was applied to a silica gel column (2×30 cm, preflushed with hexanes-triethylamine, 10:1) and eluted with 400 mL of hexanes-ethyl acetate-triethylamine (10:20:1). The product was obtained as a foam, 0.75 g (83%); $R_f$ 0.52, 0.61 (two spots on Kieselgel TLC plates, ethyl acetate-dichloromethane-triethylamine, 5:5:1). $\lambda_{max}$ (0.1M triethylammonium-acetate, pH 7.5): 234, 320 nm.

2'-Deoxy-3-Methyl-4-thiouridine.

A mixture of 1.0 g (4.23 mmol) of 2'-deoxycytidine semihydrate (Sigma) and 2.5 mL (40 mmol) of iodomethane in 5 mL of dry DMF was stirred under argon at room temperature for 24 hr. Ethyl acetate (50 mL) was added and the precipitated oil was washed three times with dry ether, dried in vacuo, and sealed into a bomb with 20 mL of water, and 45 mL of hydrogen sulfide precondensed into 15 mL of pyridine. The mixture was stirred at 60° for 64 hr. Thereafter the hydrogen sulfide was vented and trapped in 15 mL of pyridine in an i-propanol-dry ice bath. (The collected hydrogen sulfide can be reused in like reactions.) The residue from the bomb was transferred into a flask, evaporated to dryness, the residue dissolved in 10 mL of 1% acetic acid, filtered onto the top of Bakerbond C-18 column (5×33 cm) and eluted with 1 L of 1% acetic acid in 50% (v/v) methanol. Fractions with 326 nm absorbtion were combined and evaporated. The residue was dissolved in 12 mL of hot water, filtered and crystallized at 4°. The precipitate was filtered, washed with 2 mL of cold water and dried in vacuo to give 0.84 g (77%) of colorless solid, m.p. 145°–148°, $R_f$ 0.47 (Kieselgel TLC plates, ethyl acetate-acetone-methanol-water, 12:1:1:1). $\lambda_{max}$ (0.1M triethylammonium acetate, pH 7.5): 220, 326 nm. Analysis calculated for $C_{10}H_{14}N_1O_3S$: C, 46.50; H, 5.46; N, 10.85; S, 12.41%. Found: C, 46.35; H, 5.49; N, 10.74; S, 12.45%.

3-Methyl-4-thiouridine.

A mixture of 2.0 g (8.22 mmol) of cytidine (Compound 30) (Sigma) and 5 mL (80 mmol) of iodomethane in 10 mL of dry DMF was stirred under argon at room temperature for 24 hr. Ethyl acetate (100 mL) was added and the precipitated solid (3.3 g) was washed three times with dry ether, dried in vacuo, and sealed into a bomb with 20 mL of water and 45 mL of hydrogen sulfide precondensed into 15 mL of pyridine. The mixture was stirred in the sealed bomb at 60° for 64 hr, then the contents were evaporated. The residue from the bomb was transferred into a flask, evaporated further, dissolved in 10 mL of 1% acetic acid, filtered onto the top of Bakerbond C-18 column (5×33 cm) and eluted with 1 L of 1% acetic acid in 50% (v/v) methanol. Fractions with 326 nm absorbtion were combined and evaporated. The residue was dissolved in 5 mL of hot methanol, filtered and allowed to crystallize at −10°. The precipitate was filtered, washed with 2 mL of cold methanol and dried in vacuo to give 1.5 g (67%) of light yellow crystals, m.p. 146°–148°, $R_f$ 0.45 (Kieselgel TLC plates, ethyl acetate-acetone-methanol-water, 12:1:1:1). $\lambda_{max}$ (0.1M triethylammonium acetate, pH 7.5): 230, 327 nm. (Lit.: Scheit K. H. Methyl-Derivate des 4-Thiouridins. *Tetrahedron Letters*, No. 2, pp 113–118 (1967) for 3-methyl-4-thiouridine: m.p. 147°–148°; $_{max}$ (water, pH 7): 328 nm). Analysis calculated for $C_{10}H_{14}N_2O_5S$: C, 43.79; H, 5.14; N, 10.21; S, 11.69%. Found: C, 43.43; H, 5.07; N, 10.01; S, 11.56%.

3-Methyl-3',5'-O- (1,1,3,3- tetraisopropyl- 1,3-disiloxanediyl)- 4-thiouridine.

3-Methyl-4-thiouridine (1.3 g, 4.74 mmol) was separatedly taken up in pyridine and the solvent evaporated (3×10 mL), dissolved in 10 mL of dry pyridine and treated with 1.62 g of 1,3-dichloro-1,1,3,3-tetraisopropyldisiloxane at 0° for 0.5 hr and at room temperature for 1 hr. The mixture was treated with 3 mL of methanol, evaporated to dryness, the residue dissolved in 200 mL of ethyl acetate, and washed with 30 mL of saturated NaCl. The solution was dried over Na$_2$SO$_4$, evaporated and applied to silica gel column (4×25 cm), eluted with 500 mL of dichloromethane-ethanol (20:1) to afford 2.0 g (82%) of 3',5'-protected nucleoside as a solid foam, R$_f$ 0.41 (Kieselgel TLC plates, chloroform-ethanol, 20:1). $\lambda_{max}$ (0.1M triethylammonium acetate, pH 7.5): 240, 327 nm.

2',3-O,N-Dimethyl-4-thiouridine.

A solution of 2.0 g (3.87 mmol) of 3-methyl-3',5'-O-(1, 1,3,3-tetraisopropyl-1,3-disiloxanediyl)-4-thiouridine in 80 mL of ether was treated with 0.5 g (12.5 mmol) of sodium hydride (60% dispersion in oil) and 4 mL of dimethylsulfate. Water (3 drops) was added to initiate reaction. The mixture was stirred for 20 min and treated with 30 mL of 30% NH$_3$ for 4 hr. Saturated NaCl (30 mL) was added. The organic layer was separated, dried over Na$_2$SO$_4$, evaporated, and treated with 5 mL of 1M tetrabutylammonium fluoride in THF for 10 hr for deprotection. The mixture was evaporated, treated with 30 mL of 2% acetic acid and extracted with 2×10 mL of hexanes. The aqueous solution was applied to Bakerbond C-18 column (5×33 cm) and eluted with 1 L of 1% acetic acid in 50% (v/v) methanol. Fractions with 327 nm absorbtion were combined, evaporated, and dried in vacuo to give 0.54 g (48%) of crystals, m.p. 184°–187°, R$_f$ 0.44 (Kieselgel TLC plates, ethyl acetate-acetone-methanol-water, 12:1:1:1). $\lambda_{max}$, nm (0.1M triethylammonium acetate, pH 7.5): 230, 327 nm. Analysis calculated for C$_{11}$H$_{16}$N$_2$O$_5$S: C, 45.82; H, 5.59; N, 9.72; S, 11.12. Found C, 45.84; H, 5.42; N, 9.64; S, 11.12%.

2'-Deoxy-5'-O-dimethoxytrityl-3-methyl-4-thiouridine.

2'-Deoxy-3-methyl-4-thiouridine (0.60 g, 2.32 mmol) was dried by evaporation with pyridine, dissolved in 25 mL of pyridine, and treated with 0.97 g (2.86 mmol) of 4,4'-dimethoxytritylchloride for 5 hours. The mixture was treated with 5 mL of methanol, evaporated to dryness and the residue applied to a column of silica gel (2×45 cm, pre-flushed with ethyl acetate-triethylamine, 10:1). The product was eluted with 400 mL of ethyl acetate-hexanes-triethylamine (50:50:1). The yield was 1.3 g (81%), solid foam; R$_f$ 0.2 (Kieselgel TLC plates, ethyl acetate-hexanes-triethylamine (5:5:1). $\lambda_{max}$ (0.1M triethylammonium acetate, pH 7.5): 236, 327 nm.

5'-Dimethoxytrityl-2',3-O,N-dimethyl-4-thiouridine.

2',3-O,N-Dimethyl-4-thiouridine (0.67 g, 2.32 mmol) was dried by evaporation with pyridine, dissolved in 25 mL of pyridine, and treated with 0.97 g (2.86 mmol) of 4,4'-dimethoxytritylchloride for 5 hr. The mixture was treated with 5 mL of methanol, evaporated to dryness and the residue applied to a column of silica gel (2×45 cm, pre-flushed with ethyl acetate-triethylamine, 10:1). The product was eluted with 400 mL of ethyl acetate-hexanes-triethylamine (50:50:1). The yield was 1.35 g (98%), solid foam; R$_f$ 0.28 (Kieselgel TLC plates, ethyl acetate-hexanes-triethylamine (5:5:1). $\lambda_{max}$ (0.1M triethylammonium acetate, pH 7.5): 236, 327 nm. Analysis calculated for C$_{32}$H$_{34}$N$_2$O$_7$S: C, 65.07; H, 5.80; N, 4.74; S, 5.43%. Found C, 64.83; H, 6.03; N, 4.62; S, 5.29%.

2'-Deoxy-5'-O-dimethoxytrityl-3-methyl-4-thiouridine-3'-O-(2-cyanoethyl-N,N-diisopropylphosphoramidite).

A solution of 1.20 g (2.17 mmol) of 2'-Deoxy-5'-O-dimethoxytrityl-3-methyl-4-thiouridine in 55 mL of dry dichloromethane and 1.4 mL of diisopropylethylamine was treated dropwise with 0.9 mL (4.0 mmol) of 2-cyanoethyl-N,N-diisopropylchlorophosphoramidite (Aldrich), and the mixture was stirred at room temperature under argon for 2.5 hours. Methanol (0.5 mL), ethyl acetate (200 mL), and triethylamine (5 ml) were added, and the organic layer was washed successively with saturated NaHCO$_3$ (2×100 mL) and saturated NaCl (2×100 mL), dried over anhydrous Na$_2$SO$_4$ and evaporated to dryness. The residue was applied to a silica gel column (2×40 cm, preflushed with hexanes-triethylamine, 10:1) and eluted with 300 mL of hexanes-ethyl acetate-triethylamine (100:100:1). The product was obtained as a foam, 1.2 g (73%); R$_f$ 0.5, 0.6 (two spots on Kieselgel TLC plates, hexanes-ethyl acetate-triethylamine 100:100:1). $\lambda_{max}$ (0.1M triethylammonium acetate, pH 7.5): 220, 235, 328 nm.

5'-O-Dimethoxytrityl-2',3-O,N-dimethyl-4-thiouridine-3'-O-(2-cyanoethyl-N,N-diisopropylphosphoramidite).

A solution of 1.28 g (2.17 mmol) of 5'-O-dimethoxytrityl-2',3-O,N-dimethyl-4-thiouridine (24) in 55 mL of dry dichloromethane and 1.4 mL of diisopropylethylamine was treated dropwise with 0.9 mL (4.0 mmol) of 2-cyanoethyl-N,N-diisopropylchlorophosphoramidite (Aldrich), and the mixture was stirred at room temperature under argon for 2.5 hr. Methanol (0.5 mL), ethyl acetate (200 mL), and triethylamine (5 mL) were added, and the organic layer was washed successively with saturated NaHCO$_3$ (2×100 mL) and saturated NaCl (2×100 mL), dried over anhydrous Na$_2$SO$_4$ and evaporated to dryness. The residue was applied to a silica gel column (2×40 cm, preflushed with hexanes-triethylamine, 10:1) and eluted with 300 mL of hexanes-ethyl acetate-triethylamine (100:100:1). The product was obtained as a foam, 1.4 g (81%); R$_f$ 0.53 (Kieselgel TLC plates, hexanes-ethyl acetate-triethylamine 100:100:1). $\lambda_{max}$ (0.1M triethylammonium acetate, pH 7.5): 220, 235, 328 nm.

---

What is claimed is:

1. A homooligonucleotide having the formula shown below:

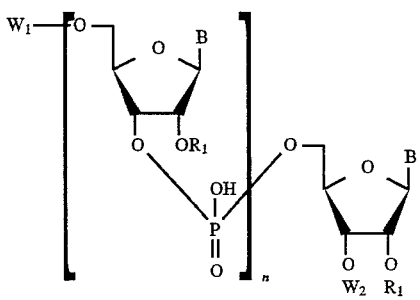

wherein n is an integer between 5 and 99;

$R_1$ is $C_1$–$C_6$alkyl or $C_2$–$C_6$alkenyl;

B is a modified heterocylic base which has the formula (1)

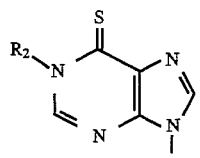

where $R_2$ is $C_1$–$C_6$alkyl;

$W_1$ is H or $Y_1O(OH)OP$—;

$W_2$ is H or $Y_2O(OH)OP$—;

$Y_1$ and $Y_2$ independently are H, $(CH_2)_mOH$, $(CH_2)_mNH_2$, a cycloalkyl group of 3 to 30 carbons; a lipophilic group selected from the group consisting of cholesterol, cholic acid, protesterone and estradiol, having an appendant connecting group attached thereto said appendant connecting group being selected from the group consisting of —S—$(CH_2)_{n'}$, —NHCO— and NH—$(CH_2)_{n'}$, NHCO— and attached to the lipophilic group by the NHCO— group, and where m is an integer between 2–25, and n' is 1 to 8.

2. A homooligonucleotide of claim 1 wherein n is in the range of 15–40.

3. A homooligonucleotide of claim 1 wherein $R_1$ is methyl.

4. A homooligonucleotide of claim 1 wherein $R_2$ is methyl.

5. A homooligonucleotide having the formula

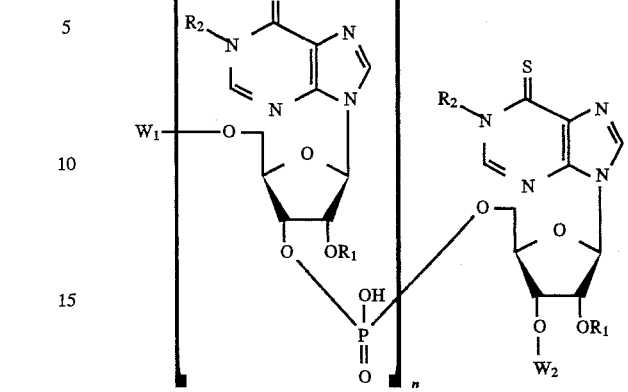

wherein n is an integer between 5 and 99;

$R_1$ is $C_1$–$C_6$alkyl or $C_2$–$C_6$alkenyl;

$R_2$ is $C_1$–$C_6$alkyl;

$W_1$ is H or $Y_1O(OH)OP$—;

$W_2$ is H or $Y_2O(OH)OP$—;

$Y_1$ and $Y_2$ independently are H, $(CH_2)_mOH$, $(CH_2)_mNH_2$, a cycloalkyl group of 3 to 30 carbons; a lipophilic group selected from the group consisting of cholesterol, cholic acid, progesterone and estradiol, having an appendant connecting group attached thereto said appendant connecting group being selected from the group consisting of —S—$(CH_2)_{n'}$, —NHCO— and NH—$(CH_2)_{n'}$, NHCO— and attached to the lipophilic group by the NHCO— group, and where m is an integer between 2–25, and n' is 1 to 8.

6. A homooligonucleotide of claim 5 wherein $R_2$ is methyl.

7. A homooligonucleotide of claim 6 wherein $R_1$ is methyl or allyl.

8. A homooligonucleotide of claim 7 wherein $W_1$ is H and $W_2$ is $Y_2O(OH)OP$— where $Y_2$ is H, $(CH_2)_mOH$ or $(CH_2)NH_2$, where m is an integer between 2 and 25.

9. A homooligonucleotide of claim 8 wherein n is an integer in the range of 15 to 40.

* * * * *